US008557534B2

(12) United States Patent
Turecek et al.

(10) Patent No.: US 8,557,534 B2
(45) Date of Patent: Oct. 15, 2013

(54) METHOD AND COMPOSITIONS FOR SPECIFICALLY DETECTING PHYSIOLOGICALLY ACCEPTABLE POLYMER MOLECULES

(75) Inventors: Peter Turecek, Klosterneuburg (AT); Juergen Siekmann, Vienna (AT); Alfred Weber, Vienna (AT); Herbert Gritsch, Vienna (AT); Katalin Varadi, Vienna (AT); Susanne Vejda, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 605 days.

(21) Appl. No.: 12/342,405

(22) Filed: Dec. 23, 2008

(65) Prior Publication Data
US 2009/0220993 A1 Sep. 3, 2009

Related U.S. Application Data

(60) Provisional application No. 61/009,327, filed on Dec. 27, 2007.

(51) Int. Cl.
*G01N 33/53* (2006.01)
*G01N 33/566* (2006.01)
(52) U.S. Cl.
USPC .............................. 435/7.9; 435/7.1; 436/501
(58) Field of Classification Search
None
See application file for complete search history.

(56) References Cited

U.S. PATENT DOCUMENTS

| | | | |
|---|---|---|---|
| 4,391,904 | A | 7/1983 | Litman et al. |
| 4,757,006 | A | 7/1988 | Toole, Jr. et al. |
| 4,970,300 | A | 11/1990 | Fulton et al. |
| 5,252,714 | A | 10/1993 | Harris et al. |
| 5,824,784 | A | 10/1998 | Kinstler et al. |
| 5,994,129 | A | 11/1999 | Armstrong et al. |
| 6,037,452 | A | 3/2000 | Minamino et al. |
| 6,048,729 | A | 4/2000 | Selden et al. |
| 6,063,630 | A | 5/2000 | Treco et al. |
| 6,379,933 | B1 | 4/2002 | Johnson et al. |
| 6,617,118 | B2 | 9/2003 | Roffler et al. |
| 7,259,224 | B2 | 8/2007 | Harris et al. |
| 7,267,941 | B2 | 9/2007 | Snell et al. |
| 2004/0014156 | A1 | 1/2004 | Roffler et al. |
| 2004/0132640 | A1 | 7/2004 | DeFrees et al. |
| 2006/0160948 | A1 | 7/2006 | Scheiflinger et al. |

FOREIGN PATENT DOCUMENTS

| | | | |
|---|---|---|---|
| WO | WO-94/15625 | | 7/1994 |
| WO | WO-94/29370 | | 12/1994 |
| WO | WO 2004/075923 | * | 9/2004 |
| WO | WO-2007/126808 | | 11/2007 |
| WO | WO-2008/082669 | | 7/2008 |

OTHER PUBLICATIONS

Abuchowski et al., "Alteration of immunological properties of bovine serum albumin by covalent attachment of polyethylene glycol", *J. Biol. Chem.*, 252:3578-81 (1977).
Caliceti et al., "Pharmacokinetic and biodistribution properties of poly(ethylene glycol)-protein conjugates", *Adv. Drug Deliv. Rev.*, 55:1261-77 (2003).
Cheng et al., "Monoclonal antibody-based quantitation of poly(ethylene glycol)-derivatized proteins, liposomes, and nanoparticles," *Bioconjugate Chem.*, 16:1225-31 (2005).
Dai et al., "Electrochemical sensor for immunoassay of carcinoembryonic antigen based on thionine monolayer modified gold electrode", *Cancer Detect Prev.*, 29:233-40 (2005).
GenBank accession No. NP_000119, platelet coagulation factor XI precursor [*Homo sapiens*], Jan. 25, 2009.
GenBank accession No. NP_000120, coagulation factor XIII A1 subunit precursor [*Homo sapiens*], Jan. 25, 2009.
GenBank accession No. NP_000121, coagulation factor V precursor [*Homo sapiens*], Mar. 1, 2009.
GenBank accession No. NP_000122, coagulation factor VII isoform a precursor [*Homo sapiens*], Mar. 1, 2009.
GenBank accession No. NP_000123, coagulation factor VIII isoform a precursor [*Homo sapiens*], Mar. 6, 2009.
GenBank accession No. NP_000124, coagulation factor IX preproprotein [*Homo sapiens*], Feb. 22, 2009.
GenBank accession No. NP_000303, protein C (inactivator of coagulation factors Va and VIIIa) [*Homo sapiens*], Mar. 1, 2009.
GenBank accession No. NP_000479, serpin peptidase inhibitor, clade C, member 1 [*Homo sapiens*], Feb. 21, 2009.
GenBank accession No. NP_000495, coagulation factor X preproprotein [*Homo sapiens*], Feb. 15, 2009.
GenBank accession No. NP_000496, coagulation factor XII precursor [*Homo sapiens*], Feb. 15, 2009.
GenBank accession No. NP_000497, coagulation factor II preproprotein [*Homo sapiens*], Mar. 1, 2009.
GenBank accession No. NP_000543, von Willebrand factor preproprotein [*Homo sapiens*], Mar. 15, 2009.
GenBank accession No. NP_001985, coagulation factor XIII B subunit precursor [*Homo sapiens*], Feb. 1, 2009.
Ghindilis, "Direct electron transfer catalysed by enzymes: application for biosensor development", *Biochem. Soc. Trans.*, 28:84-9 (2000).
Henikoff et al., "Amino acid substitution matrices from protein blocks", *Proc. Natl. Acad. Sci. USA*, 89:10915-9 (1992).
Hofmann et al., "Recent advances in the application of expressed protein ligation to protein engineering", *Curr. Opin. Biotechnol.*, 13:297-303 (2002).
Karlin et al., "Applications and statistics for multiple high-scoring segments in molecular sequences", *Proc. Natl. Acad. Sci. USA*, 90:5873-7 (1993).
Kozlowski et al., "Development of pegylated interferons for the treatment of chronic hepatitis C", *BioDrugs*, 15:419-29 (2001).
Lankhof et al., "von Willebrand factor without the A2 domain is resistant to proteolysis", *Thromb. Haemost*, 77:1008-13 (1997).
Lowe, "Factor IX and thrombosis", *Br. J. Haematol.*, 115:507-13 (2001).
Nag et al., "A colorimetric estimation of polyethyleneglycol-conjugated phospholipid in stealth liposomes", *Anal. Chem.*, 250:35-43 (1997).

(Continued)

*Primary Examiner* — Shafiqul Haq
*Assistant Examiner* — Galina Yakovleva
(74) *Attorney, Agent, or Firm* — Marshall, Gerstein & Borun LLP

(57) ABSTRACT

The present invention relates to a method for determining the amount of a physiologically acceptable polymer molecule bound to a protein, an antibody or other composition being capable of specifically binding to a physiologically acceptable polymer molecule, and a kit containing said antibody or composition.

14 Claims, 23 Drawing Sheets

(56) References Cited

OTHER PUBLICATIONS

Naser, "Single incubation multilayer immune technique", *J. Immunol. Methods*, 129:151-7 (1990).
Ouchi et al., *Polymer Preprints*, 38:582-3 (1997).
Partial International Search Report for corresponding International Application No. PCT/US2008/088131, dated Apr. 22, 2009.
Perlman et al., "Glycosylation of an N-terminal extension prolongs the half-life and increases the in vivo activity of follicle stimulating hormone", *J. Clin. Endocrinol. Metab.*, 88:3227-35 (2003).
Pietu et al., "Production in *Escherichia coli* of a biologically active subfragment of von Willebrand factor corresponding to the platelet glycoprotein Ib, collagen and heparin binding domains", *Biochem. Biophys Res. Commun.*, 164:1339-47 (1989).
Pitas et al., "Anti-phencyclidine monoclonal antibody binding capacity is not the only determinant of effectiveness, disproving the concept that antibody capacity is easily surmounted", *Drug Metab. Dispos.*, 34:906-12 (2006).
Pitkin et al., "Charge and lipophilicity govern the pharmacokinetics of glycopeptide antibiotics", *Antimicrob. Agents Chemother.*, 29:440-4 (1986).
*Remington's Pharmaceutical Sciences*, 19th ed., Easton, Pa: Mack Publishing Co. (1995).
Richter et al., "Antibodies against polyethylene glycol produced in animals by immunization with monomethoxy polyethylene glycol modified proteins", *Int. Arch. Allergy Appl. Immunol.*, 70:124-31 (1983).
Saenko et al., "Strategies towards a longer acting factor VIII", *Haemophilia*, 12 Suppl 3: 42-51 (2006).
Schultz et al., "Single-target molecule detection with nonbleaching multicolor optical immunolabels", *Proc. Natl. Acad. Sci. USA*, 97:996-1001 (2000).
Tsai et al., "Sensitive measurement of polyethylene glycol-modified proteins," *Biotechniques*, 30:396-402 (2001).
Vehaskari et al., "Glomerular charge and urinary protein excretion: effects of systemic and intrarenal polycation infusion in the rat", *Kidney Int.*, 22:127-35 (1982).
Wood et al., "Expression of active human factor VIII from recombinant DNA clones", *Nature*, 312:330-7 (1984).
Wunderlich et al., "Generation and characterization of a monoclonal IgG antibody to polyethylene glycol," *Hybridoma*, 26:168-72 (2007).

\* cited by examiner

☐ antiserum 3 weeks after immunization
(plate-immobilized PEGylated rVWF)

○ rabbit plasma before immunization
(plate-immobilized rVWF)

Inhibition of the rVWF-PEG ELISA with PEG 5000

Dose-response curves of the PEG-PEG ELISA

Specificity of the PEG-PEG ELISA

Robustness of the PEG-protein ELISA as shown with stable PEGylated rVWF

Robustness of the PEG-protein ELISA as shown with releasable PEGylated rVWF

Specificity of the PEG-protein ELISA for protein-bound PEG as shown with PEGylated rVWF Specificity of the PEG-rFVIII ELISA

Influence of different anti-FVIII peroxidase conjugates on the assay performance

Figure 14.
PEG-rFVIII ELISA in the plasma of FVIII-deficient mice and in rat plasma
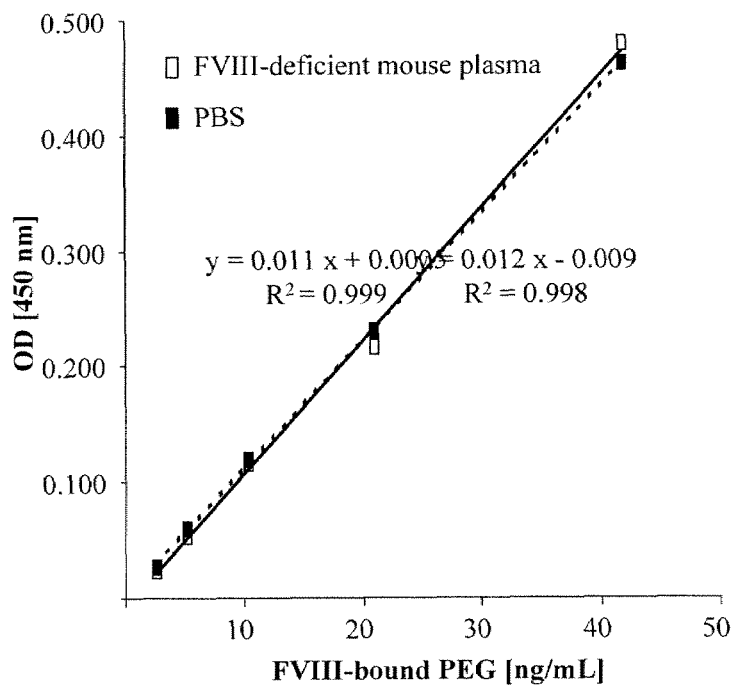
Figure 14A
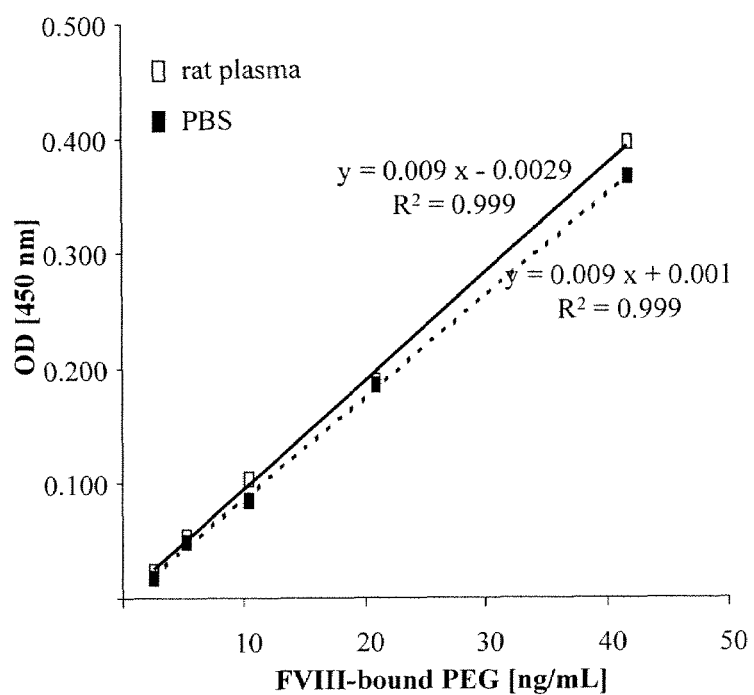
Figure 14B Measurement of PEGylated rFVIII preparations with different degree of PEGylation Influence of free PEG on the PEG-rFVIII ELISA Measurement of PEG release from a releasable PEGylated rFVIII preparation Figure 21A
Figure 21B
Stable PEG-FVIII, PD = 3.7
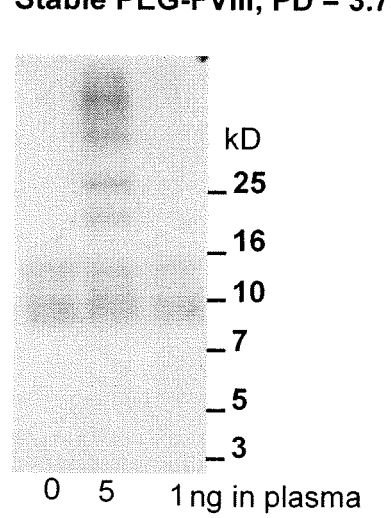
0   5    1 ng in plasma
Releasable PEG-FVIII, PD = 6
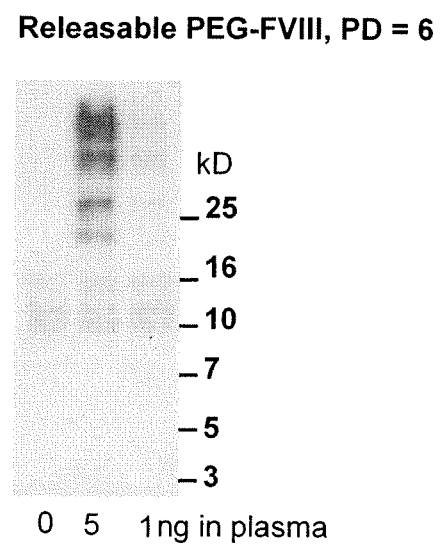
0   5    1 ng in plasma

METHOD AND COMPOSITIONS FOR SPECIFICALLY DETECTING PHYSIOLOGICALLY ACCEPTABLE POLYMER MOLECULES

This application claims the priority benefit of U.S. Provisional Patent Application No. 61/009,327, filed Dec. 27, 2007, which is incorporated herein by reference.

FIELD OF THE INVENTION

The present invention relates to a method for determining the amount of a physiologically acceptable polymer molecule bound to a protein, an antibody being capable of specifically binding to a physiologically acceptable polymer molecule, and a kit containing said antibody.

BACKGROUND OF THE INVENTION

The in vivo function of a protein is improved by binding it to a physiologically acceptable polymer molecule. In particular, binding a physiologically active protein to a physiologically acceptable polymer molecule has been found to substantially prolong its in vivo half-life. For example, U.S. Pat. No. 4,970,300 describes that the conjugation of a physiologically acceptable polymer molecule to factor VIII results in a factor VIII protein being activable by thrombin and having a substantially decreased antigenicity and immunoreactivity and a substantially increased in vivo disappearance time in the bloodstream of a mammal.

U.S. Pat. No. 4,970,300 describes that the conjugation of a polymer molecule (dextran) to Factor VIII (FVIII) results in a FVIII protein activatable by thrombin, and having a substantially decreased antigenicity and immunoreactivity and a substantially increased in vivo retention time in the bloodstream of a mammal. International patent application WO 94/15625 describes that conjugating factor VIII to a physiologically acceptable polymer molecule improves the in vivo function of factor VIII (i) by increasing its resistance to in vivo hydrolysis and thus prolonging its activity after administration, (ii) by significantly prolonging its circulating life in vivo over unmodified protein, and (iii) by increasing its absorption time into the blood stream. U.S. Pat. No. 6,037,452 describes FVIII and Factor IX (FIX) conjugates, where the protein is covalently bound to a poly(alkylene oxide) through carbonyl-groups in the protein. Further, improving the in vivo function of factor IX by binding it to physiologically acceptable polymer molecules, in particular poly(ethylene glycol) ("PEG"), has been described in international patent application WO 94/29370. A PEGylated FVIII that retains specific activity was disclosed in International Patent Publication WO/2007/126808. The conjugation of physiologically acceptable polymer to an active agent such as a protein is performed by preparing stable polymer-protein conjugates or polymer-protein conjugates in which the physiologically acceptable polymer is attached to the protein via releasable covalent bonds (pro-drug concept), i.e. a hydrolyzable or releaseable linker. For example, a releasable PEG moiety has been developed using a 9-flourenemethoxycarbonyl (FMOC) conjugation system containing two PEG chains (Nektar Inc., Huntsville Ala.). In addition an N-hydroxysuccinimide ester (NHS) group, which is useful for the chemical modification of lysine residues of the protein, may be linked to the fluorene ring system via the methoxycarbonyl group to generate the releasable PEG moiety. International Patent Publication WO 2008/082669 (incorporated herein by reference) describes a series of PEGylated recombinant FVIII variants based on the releasable PEG concept.

However, at present no reliable method for the quantitative determination of physiologically acceptable polymer molecules bound to proteins or nanoparticles is available apart from insensitive calorimetric methods (Nag et al. 1997, Anal Biochem 250:35-43), which allow only an estimation of the content of physiologically acceptable polymer molecules. Moreover, monoclonal antibodies for the determination of PEG concentrations have been disclosed (U.S. Pat. No. 6,617,118), but so far no system is available for the reliable determination of the amount of physiologically acceptable polymer molecule bound to a protein.

Therefore, a need exists for a new system to determine the amount of a physiologically acceptable polymer molecule, in particular PEG, bound to a protein, particularly a physiologically active protein.

SUMMARY OF THE INVENTION

The present invention relates to a method for determining the amount of a physiologically acceptable polymer molecule bound to a protein. Additionally, an antibody being capable of specifically binding to a physiologically acceptable polymer molecule wherein for example said polymer molecule is present bound to a protein is provided according to the present invention. Further, the present invention relates to the use of said antibody for determining the amount of a physiologically acceptable polymer molecule bound to a protein.

In one aspect, the invention provides a method for determining the amount of a physiologically acceptable polymer molecule bound to a protein, comprising the steps of: (a) providing at least one protein bound to at least one physiologically acceptable polymer molecule; (b) providing at least one antibody being capable of specifically binding to said physiologically acceptable polymer molecule; (c) bringing the antibody of step (b) into contact with the protein of step (a) under conditions suitable for binding said antibody to the at least one polymer molecule bound to said protein; and (d) detecting a formation of a complex between the antibody and the physiologically acceptable polymer molecule.

In one embodiment, in step (a) the protein bound to at least one physiologically acceptable polymer molecule is immobilized on a substrate or carrier matrix.

In a further embodiment, the antibody is selected from the group consisting of a polyclonal antibody and a monoclonal antibody.

In another embodiment, the protein is von Willebrand factor (VWF) or a derivative thereof. In a further embodiment, the protein is Factor VIII or a derivative thereof.

In some embodiments, the physiologically acceptable polymer molecule is selected from the group consisting of poly(alkylene glycol), poly(propylene glycol), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphasphazene, polyoxazoline, and poly(N-acryloylmorpholine). In a related embodiment, the physiologically acceptable polymer molecule is poly(ethylene glycol) (PEG) or a derivative thereof.

In another aspect, the invention contemplates, an antibody being capable of specifically binding to a physiologically acceptable polymer molecule. In one embodiment, the antibody is a polyclonal antibody.

In a related embodiment, physiologically acceptable polymer molecule is bound to a protein. In a further embodiment, the protein is von Willebrand factor (VWF) or a derivative thereof. In another embodiment, the physiologically acceptable polymer molecule is selected from the group consisting of poly(alkylene glycol), poly(propylene glycol), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(☐-hydroxy acid), poly(vinyl alcohol), polyphosphaszhene, polyoxazoline, and poly(N-acryloylmorpholine). In a related embodiment, the physiologically acceptable polymer molecule is poly(ethylene glycol) (PEG) or a derivative thereof.

In a further aspect, the invention provides a kit for determining the amount of a physiologically acceptable polymer molecule bound to a protein, comprising an antibody as described herein.

In another aspect, the invention provides a method for determining the number of physiologically acceptable polymer molecules bound to a protein or protein complex in a polymer-protein conjugate, comprising the steps of detecting binding between (i) a polymer:protein conjugate having one or more polymers bound to the protein and (ii) an antibody that specifically binds said polymer, said antibody detectable when bound to said polymer:protein conjugate, wherein the number of polymers in the polymer:protein conjugate correlates with levels of antibody detected bound to the polymer:protein conjugate when compared to a known control.

In one embodiment, the antibody comprises a detectable label. In a related embodiment, the detectable label is selected from the group consisting of an enzyme, a radioactive label, a fluorophore, an electron dense reagent, biotin, digoxigenin, haptens, and proteins which are made detectable by addition of any of these labels.

In a further embodiment, the polymer:protein conjugate is bound to a carrier matrix prior to binding with the antibody. In certain embodiments, the carrier matrix is selected from the group consisting of a microcarrier, a particle, a membrane, a strip, paper, a film, a bead or a plate. In a related embodiment, the polymer:protein conjugate is isolated using sodium dodecylsulfate polyacrylamide gel electrophoresis (SDS-PAGE) and transferred to a membrane prior to the detecting. In a further embodiment, the molecular weight of the polymer-protein complex correlates with the protein subunit comprising the polymer molecule.

In yet another embodiment, the level of antibody detected is measured as absorbance of the detectable label. In a related embodiment, the number of polymers in the polymer:protein conjugate is calculated based on the molecular weight of the protein-polymer conjugate compared to a known control. Exemplary methods to measure polymer molecules for a known control include, but are not limited to size exclusion chromatography, high performance liquid chromatography (HPLC) and mass spectrometry.

In one embodiment of the invention, the protein or protein complex is a blood clotting factor or a blood clotting factor complex. In a related embodiment, the blood clotting factor or blood clotting factor complex is human. In a still further embodiment, the blood clotting factor is selected from the group consisting of Factor II, Factor V, Factor VII, Factor VIII, Factor IX, Factor X, Factor XI, Factor XII, Factor XIII, von Willebrand Factor, protein C, antithrombin III, and activated forms thereof. In another embodiment, the blood clotting factor complex is FactorVIII:VWF.

In certain embodiments, the polymer is releasable. In a related embodiment, the polymer is hydrolyzable. In one embodiment, the physiologically acceptable molecule is attached to the protein or protein complex via a linker.

In one embodiment, the polymer is selected from the group consisting of poly(alkylene glycol), poly(propylene glycol), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(hydroxy acid), such as poly(α-hydroxy acid) and poly(β-hydroxy acid), poly(vinyl alcohol), polyphosphaszhene, polyoxazoline, and poly(N-acryloylmorpholine).

In a related embodiment, the polymer is polyethylene glycol (PEG) or a derivative thereof. In another embodiment, the PEG is from about 3 to about 200 kDa. In a further embodiment, the PEG has a molecular weight in a range of about 5 kDa to about 60 kDa. In another embodiment, the PEG has a molecular weight in a range of about 5 kDa to about 40 kDa. In still another embodiment, the PEG has a molecular weight in a range of about 5 kDa to about 15 kDa. And in a still further embodiment, the PEG has a molecular weight in a range of about 5 kDa to about 10 kDa. Additional PEG compositions contemplated for use herein include, but are not limited to, PEG in the range of from about 5 to about 150 kDa, about 5 to about 120 kDa, from about 10 to about 100 kDa, from about 20 to about 50 kDa, and from about 5 to about 25 kDa, as well as PEG having a molecular weight of about 5 kDa, about 10 kDa, about 15 kDa, about 20 kDa, about 25 kDa, is about 30 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa, about 100 kDa, about 110 kDa, about 120 kDa, about 130 kDa, about 140 kDa, about 150 kDa, about 160 kDa, about 170 kDa, about 180 kDa, about 190 kDa, or about 200 kDa.

In another aspect, the invention provides a method for determining the number of physiologically acceptable polymer molecules bound to a protein or a protein complex or free in solution comprising, contacting said polymer with an antibody that specifically binds said polymer, said antibody detectable when bound to said polymer, wherein the number of polymers bound by the antibody correlates with levels of antibody detected bound when compared to a known control.

In a related aspect, the invention contemplates a method for determining the number of physiologically acceptable polymer molecules bound to a protein or a protein complex, contacting said protein or protein complex with an antibody that specifically binds said protein or protein complex, said antibody detectable when bound to said protein or protein complex, wherein the number of polymers bound by the antibody correlates with levels of antibody detected bound when compared to a known control.

In related embodiments, the method of the invention is carried out using an ELISA technique. It is contemplated that the ELISA reagents are used as follows, wherein the first antibody listed is the antibody bound to the substrate and the second antibody bound in the antibody that is detectable. Exemplary assays useful to detect the number of polymers bound to a protein or protein complex include an anti-polymer-anti-protein detection method, an anti-protein-anti-polymer detection method, or an anti-polymer-anti-polymer detection method, wherein the anti-polymer antibody is the same antibody for each binding step, or is a different polymer-specific antibody for each step. In a related embodiment, the assay is carried out using only an anti-polymer specific antibody or an anti-protein-specific antibody.

BRIEF DESCRIPTION OF THE FIGURES

FIG. 14 shows the detection of PEG-rFVIII ELISA in the plasma of FVIII-deficient mice and in rat plasma.

FIG. 21 shows that the method is able to differentiate between degrees of PEGylation (FIG. 4A, PD=3.7, FIG. 4B, PD=6), wherein a higher PEGylation degree resulted in a stronger signal.

DETAILED DESCRIPTION OF THE INVENTION

Figure 1A:
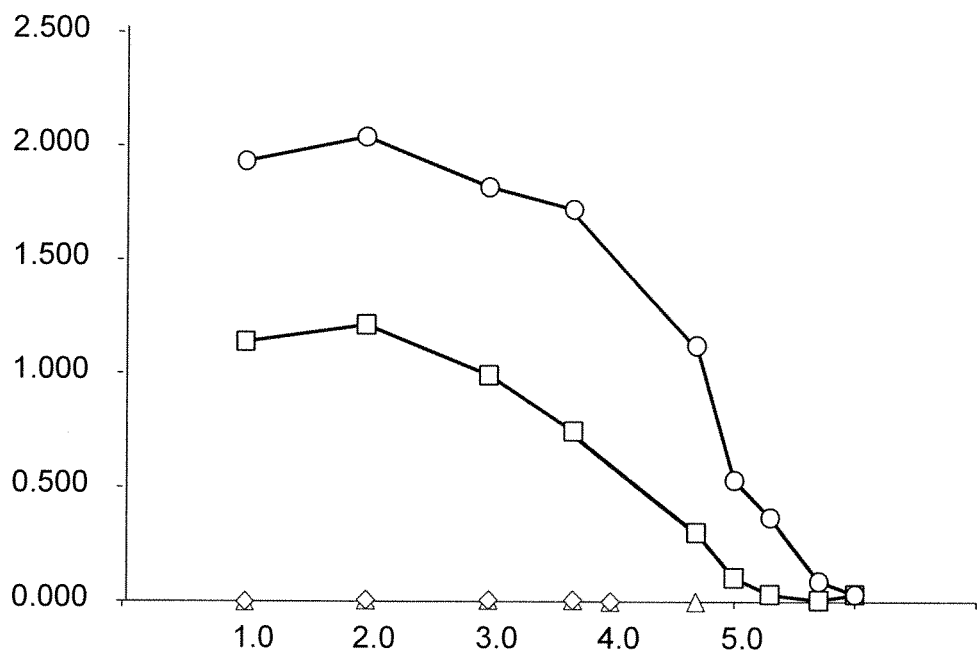
FIG. 1 shows a direct Enzyme Linked Immunosorbent Assay (ELISA) on the antigen HSAP-2-SS (PEGylated human serum albumin (hSA)). Rabbits were inoculated with preparations of the antigen HSAP-2-h-SS having about 380 µg/ml protein and a PEG concentration of 250 µg/ml. Serum samples of all animals were taken before the start and after 3 and 4 weeks and were subsequently tested for detectable antibody formation against the antigen HSAP-2-h-SS. The antigen HSAP-2-h-SS is coated on a surface in 0.1 M carbonate at pH 9.6 at 1 µg ml. The samples are diluted in PBS-gelatin buffer and incubated with the wells and subsequently with a goat anti-rabbit IgG-HRP antibody using Single Incubation Multilayer Immune Technique (SIMIT). The optical density (OD) (vertical axis) is shown for the log dilution (horizontal axis) of the respective samples. ▲ SPF (normal rabbit serum); ♦, Pool 0 (4 animals before); ■, Pool 3 weeks (4 animals); ●, Pool 4 weeks (4 animals).

The present invention is directed to methods for determining the amount of a physiologically acceptable polymer molecule bound to a protein.

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that, as used in this specification and the appended claims, the singular forms "a," "an," and "the" include plural reference unless the context clearly dictates otherwise.

As used herein, the following terms have the meanings ascribed to them unless specified otherwise.

The term "sample" as used herein refers to any sample containing at least one protein bound to at least one physiologically acceptable polymer molecule, such as any fluid or solution originating from a process for preparing pharmaceutical products.

The term "protein" as used herein refers to any protein, protein complex or polypeptide, including recombinant proteins, protein complexes and polypeptides composed of amino acid residues linked via peptide bonds. Proteins may be obtained by isolation of a protein from in vivo, by synthetic methods or obtained via recombinant DNA technology. Synthetic polypeptides are synthesized, for example, using an automated polypeptide synthesizer. A recombinant protein used according to the present invention may be produced by any method known in the art as described herein below. In one embodiment, the protein is a physiologically active protein, including a therapeutic protein or a biologically active derivative thereof. The term "biologically active derivative" refers to a modification of a protein having substantially the same functional and/or biological properties of the parent protein. The term "protein" typically refers to large polypeptides. The term "peptide" typically refers to short polypeptides. As used herein, polypeptide, protein and peptide are used interchangeably. A "protein complex" refers to a molecule that is comprised of at least one protein bound to at least one other protein. Examples of protein complexes include, but are not limited to, a protein bound to a cofactor or chaperone protein, ligand-receptor complexes and multisubunit proteins such as integrins and other cell surface receptors comprises of multiple protein subunits.

As used herein a "fragment" of a polypeptide refers to any portion of the polypeptide smaller than the full-length polypeptide or protein expression product. Fragments are typically deletion analogs of the full-length polypeptide wherein one or more amino acid residues have been removed from the amino terminus and/or the carboxy terminus of the full-length polypeptide. Accordingly, "fragments" are a subset of deletion analogs described below.

As used herein an "analog" or "derivative" (which may be used interchangeably) refers to a polypeptide substantially similar in stricture and having the same biological activity, albeit in certain instances to a differing degree, to a naturally-occurring molecule. Analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence, (ii) insertion or addition of one or more amino acids at one or more termini (typically an "addition" analog) of the polypeptide and/or one or more internal regions (typically an "insertion" analog) of the naturally-occurring polypeptide sequence or (iii) substitution of one or more amino acids for other amino acids in the naturally-occurring polypeptide sequence. Substitutions are conservative or non-conservative based on the physico-chemical or functional relatedness of the amino acid that is being replaced and the amino acid replacing it.

In one aspect, an analog exhibits about 70% sequence similarity but less than 100% sequence similarity with a given compound, e.g., a peptide. Such analogs or derivatives are, in one aspect, comprised of non-naturally occurring amino acid residues, including by way of example and not limitation, homoarginine, ornithine, penicillamine, and norvaline, as well as naturally occurring amino acid residues. Such analogs or derivatives are, in another aspect, composed of one or a plurality of D-amino acid residues, or contain non-peptide interlinkages between two or more amino acid residues. The term "derived from" as used herein refers to a polypeptide or peptide sequence that is a modification (including amino acid substitution or deletion) of a wild-type or naturally-occurring polypeptide or peptide sequence and has one or more amino acid substitutions, additions or deletions, such that the derivative sequence shares about 70% but less than 100% sequence similarity to the wild-type or naturally-occurring sequence. In one embodiment, the derivative may be a fragment of a polypeptide, wherein the fragment is substantially homologous (i.e., at least 70%, at least 75%, at least 80%, at least 85%, at least 90%, or at least 95% homologous) over a length of at least 5, 10, 15, 20, 25, 30, 35, 40, 45 or 50 amino acids of the wild-type polypeptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison is conducted, in certain embodiments, by the local homology algorithm of Smith & Watennan, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection. One example of a useful algorithm is PILEUP, which uses a simplification of the progressive alignment method of Feng & Doolittle, J. Mol. Evol. 35:351-360 (1987) and is similar to the method described by Higgins & Sharp, CABIOS 5:151-153 (1989). Another algorithm useful for generating multiple alignments of sequences is Clustal W (Thompson et al., Nucleic Acids Research 22: 4673-4680 (1994)). An example of algorithm that is suitable for determining percent sequence identity and sequence similarity is the BLAST algorithm (Altschul et al., J. Mol. Biol. 215:403-410 (1990); Henikoff & Henikoff, Proc. Natl. Acad. Sci. USA 89:10915 (1989); Karlin & Altschul, Proc. Natl. Acad. Sci. USA 90:5873-5787 (1993)). Software for performing BLAST analyses is publicly available through the National Center for Biotechnology Information.

Substitutions are conservative or non-conservative based on the physico-chemical or functional relatedness of the amino acid that is being replaced and the amino acid replacing it. Substitutions of this type are well known in the art. Alternatively, the invention embraces substitutions that are also non-conservative. Exemplary conservative substitutions are described in Lehninger, [Biochemistry, 2nd Edition; Worth Publishers, Inc., New York (1975), pp. 71-77] and set out below.

Conservative Substitutions

| SIDE CHAIN CHARACTERISTIC | AMINO ACID |
|---|---|
| Non-polar (hydrophobic): | |
| A. Aliphatic | A L I V P |
| B. Aromatic | F W |

-continued

| SIDE CHAIN CHARACTERISTIC | AMINO ACID |
|---|---|
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternatively, exemplary conservative substitutions are set out immediately below.

Conservative Substitutions II

| ORIGINAL RESIDUE | EXEMPLARY SUBSTITUTION |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

As used herein a "variant" refers to a protein or analog thereof that is modified to comprise additional chemical moieties not normally a part of the molecule. Such moieties improve, in various aspects, the molecule's solubility, absorption, biological half-life, etc. The moieties alternatively decrease the toxicity of the molecule and eliminate or attenuate any undesirable side effect of the molecule, etc. Moieties capable of mediating such effects are disclosed in Remington's Pharmaceutical Sciences (1980). Procedure for coupling such moieties to a molecule are well known in the art. In certain aspects, without limitation, variants are polypeptides that are modified by glycosylation, PEGylation, or polysialylation.

As used herein, "naturally-occurring," as applied to a protein or polypeptide, refers to a protein found in nature. For example, a polypeptide or polynucleotide sequence that is present in an organism (including viruses) that are isolated from a source in nature and which has not been intentionally modified by man in the laboratory is naturally-occurring. The terms "naturally-occurring" and "wild-type" are used interchangeably throughout.

As used herein, "plasma-derived," as applied to a protein or polypeptide, refers to a naturally-occurring polypeptide or fragment thereof that is found in blood plasma or serum of a subject.

The term "physiologically acceptable polymer molecule" as used herein refers to polymer molecules which are substantially soluble in aqueous solution or may be present in form of a suspension and have substantially no negative impact to mammals upon administration of a polymer-protein conjugate in a pharmaceutically effective amount and are regarded as biocompatible. In one embodiment, physiologically acceptable molecules comprise from 2 to about 1000, or from about 2 to about 300 repeating units. Exemplary physiologically acceptable polymers include, but are not limited to, poly(alkylene glycols) such as polyethylene glycol (PEG), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), poly(alkylene oxide) polymers, poly(maleic acid), poly(DL-alanine), polysaccharides, such as carboxymethylcellulose, dextran, hyaluronic acid and chitin, poly(meth)acrylates, and combinations of any of the foregoing.

The physiologically acceptable polymer molecule is not limited to a particular structure and, in certain aspects, is linear (e.g. alkoxy PEG or bifunctional PEG), branched or multi-armed (e.g. forked PEG or PEG attached to a polyol core), dendritic, or with degradable linkages. Moreover, the internal structure of the polymer molecule are, in still other aspects, organized in any number of different patterns and are selected from the group consisting of, without limitation, homopolymer, alternating copolymer, random copolymer, block copolymer, alternating tripolymer, random tripolymer, and block tripolymer.

The term "linker" refers to a molecular fragment that links the physioloigically acceptable polymer to a biologically active molecule. The fragment typically has two functional groups that can be coupled to or activated to react with another linker or directly with the biologically active nucleophile. As an example, ω-aminoalkanoic acid such as lysine is commonly used. In the present invention, linkers includes stable, releasable and hydrolyzable linkers.

The expression "protein bound to at least one physiologically acceptable polymer molecule" as used herein includes a protein covalently bound or non-covalently bound by interactions such as ionic, hydrophobic, affinity, bioaffinity interactions, to one or more polymer molecules. In various embodiments, the polymer molecule is coupled to the protein by use of bifunctional reagents and via a spacer arm. In addition, the polymer molecule is coupled to the protein by affinity interaction. For example, the protein, in certain embodiments, is biotinylated and avidin or streptavidin conjugated polymer molecules can be bound to the protein. Further, polyclonal or monoclonal antibodies as well as fragments thereof are bound to a polymer molecule, and then this complex can be bound to the protein. Polymer molecules are also bound to the protein also by enzymatic methods such as, for example, the transfer of saccharides with polyglycosyltransferase (U.S. Pat. No. 6,379,933) or glycopegylation (US 2004 0132640). Another approach is the binding of polymer molecules to the protein on the basis of their biological function, like for example the binding of PEGylated collagens or collagen fragments to the A1 and A3 domains of the VWF protein. For this purpose, in some embodiments, collagens from type I and III, e.g. from human placenta, showing a strong interaction with the VWF are used. In certain embodiments, the binding of the polymer molecule is irreversible or reversible under physiological conditions after an in vivo-application of the protein.

The term "PEGylated" as used herein refers to a protein, protein complex or polypeptide bound to one or more PEG moieties. The term "PEGylation" as used herein refers to the process of binding one or more PEGs to a protein. In one embodiment, the molecular weight of said PEG is in the range of from 3 to 200 kDa, from 5 to 120 kDa, from 10 to 100 kDa, from 20 to 50 kDa, from 5 to 60 kDA, from 5 to 40 kDa, from 5 to 25 kDa, from 5 to 15 kDa, or from 5 to 10 kDa.

The term "specifically binds" or is "specific for" a physiologically acceptable polymer refers to the ability of a binding agent to recognize and bind a physiologically acceptable polymer, but not other compounds (or other antigens). For example, an antibody "specific for" its cognate antigen indicates that the variable regions of the antibodies recognize and bind the compound of interest with a detectable preference (i.e., able to distinguish the compound of interest from other known compounds of the similar structure or composition, by virtue of measurable differences in binding affinity, despite the possible existence of localized sequence identity or homology if the antibody is specific for a polypeptide, or similarity between compounds). It will be understood that specific antibodies may also interact with other proteins (for example, S. aureus protein A or other antibodies in ELISA techniques) through interactions with sequences outside the variable region of the antibodies, and in particular, in the constant region of the molecule. Screening assays to determine binding specificity of an antibody for use in the methods of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies for use in the invention can be produced using any method known in the art.

A "detectable label" or a "detectable moiety" is a composition detectable by spectroscopic, photochemical, biochemical, immunochemical, chemical, or other physical means. For example, labels suitable for use in the present invention include, for example, radioactive labels (e.g., $^{32}P$), fluorophores (e.g., fluorescein), electron dense reagents, enzymes (e.g., as commonly used in an ELISA), biotin, digoxigenin, or haptens and proteins which are made detectable, e.g., by incorporating a radiolabel into the hapten or peptide, or used to detect antibodies specifically reactive with the hapten or peptide.

The term "substrate" or "carrier matrix" does not mean any specific limitations, and relates, for example, to an insoluble polymer material, which can be an organic polymer, such as polyamide or a vinyl polymer (e.g. poly(meth)acrylate, polystyrene and polyvinyl alcohol, or derivatives thereof), a natural polymer such as cellulose, dextrane, agarose, chitin and polyamino acids, or an inorganic polymer, such as glass or metallohydroxide. In certain embodiments, the substrate is in the form of a microcarrier, particles, membranes, strips, paper, film, pearls, beads or plates, such as microtiter plates. In one aspect, the protein bound to at least one physiologically acceptable polymer molecule is immobilized on the substrate directly by covalent coupling or via a carrier such as a linker molecule or an antibody immobilized on the substrate.

"Pharmaceutical composition" refers to a composition suitable for pharmaceutical use in subject animal, including humans and mammals. A pharmaceutical composition comprises a pharmacologically effective amount of a polymer-polypeptide conjugate and also comprises a pharmaceutically acceptable carrier. A pharmaceutical composition encompasses a composition comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound or conjugate of the present invention and a pharmaceutically acceptable carrier.

"Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). A "pharmaceutically acceptable salt" is a salt that is formulated into a compound or conjugate for pharmaceutical use including, e.g., metal salts (sodium, potassium, magnesium, calcium, etc.) and salts of ammonia or organic amines.

"Pharmaceutically acceptable" refers to a material which is not biologically or otherwise undesirable, i.e., the material may be administered to an individual without causing any undesirable biological effects or interacting in a deleterious manner with any of the components of the composition in which it is contained.

One aspect of the present invention relates to a method for determining the amount of a physiologically acceptable polymer molecule bound to a protein, comprising the steps of:

(a) providing at least one protein bound to at least one physiologically acceptable polymer molecule;

(b) providing at least one antibody being capable of specifically binding to said physiologically acceptable polymer molecule;

(c) bringing the antibody of step (b) into contact with the protein of step (a) under conditions suitable for binding said antibody to the at least one polymer molecule bound to said protein; and (d) detecting a formation of a complex between the antibody and the physiologically acceptable polymer molecule.

The complex between the antibody and the polymer molecule is detected by methods well known in the art. Examples for the detection of the above mentioned complex include, but are not limited to, the use of a labelled antibody directed against the antibody being capable of specifically binding to the physiologically acceptable polymer molecule or the antibody being capable of specifically binding to a physiologically acceptable polymer molecule is covalently linked to a detectable label which is any suitable detectable label known in the art. The detection method for measuring the detectable label is, for example, and without limitation, selected from the group consisting of an enzyme assay, a chromogenic assay, a lumino assay, a fluorogenic assay, and a radioimmune assay. The reaction conditions to perform detection of the detectable label depend upon the detection method selected. It is within the knowledge of the person skilled in the art to choose the optimal parameters, such as buffer system, temperature and pH for the respective detection system to be used.

The quantification of the detectable label resulting in the determination of the amount of the physiologically acceptable polymer molecules bound to the protein is carried out by standard methods. For example, in one aspect, the antibody being capable of specifically binding to the physiologically acceptable polymer molecule is conjugated to an enzyme (e.g., a peroxidase), and for detection, an enzymatic substrate reaction is carried out. The amount of physiologically acceptable polymer molecules is calculated from a calibration curve obtained by a protein of interest bound to the physiologically acceptable polymer molecules defined amounts. The amounts of physiologically acceptable polymer molecules bound to the protein of interest can are obtained, for example, by evaluating data from SDS-gel electrophoresis and determining the mass increase after binding of the physiologically acceptable polymer molecules.

In one aspect, the antibody according to the present invention is selected from the group consisting of a polyclonal antibody, a chimeric antibody, a monoclonal antibody derived by conventional hybridoma techniques, and an antibody or antibody fragment obtained by recombinant techniques, e.g. phage display or ribosome display. In one embodiment of the present invention, the antibody is a polyclonal antibody.

According to the present invention, the term "protein" does not underlie a specific restriction and may include any protein, protein complex or polypeptide, including recombinant proteins, protein complexes and polypeptides obtained via recombinant DNA technology. The recombinant protein used according to the present invention may be produced by any method known in the art. This may include any method known in the art for (i) the production of recombinant DNA by genetic engineering, e.g. via reverse transcription of RNA and/or amplification of DNA, (ii) the introduction of recombinant DNA into prokaryotic or eukaryotic cells by transfection, e.g. via electroporation or microinjection, (iii) the cultivation of said transformed cells, e.g. in a continuous or batchwise manner, (iv) the expression of the protein, e.g. constitutive or upon induction, and (v) the isolation of the protein, e.g. from the culture medium or by harvesting the transformed cells, in order to (vi) obtain purified recombinant protein, e.g. via anion exchange chromatography or affinity chromatography.

Proteins and Protein Complexes

Proteins contemplated for use in the compositions include physiologically active proteins useful for administration to a subject. In one embodiment, the physiologically active protein is a therapeutic protein. The physiologically active protein, is in one aspect, a protein or any fragment of such that still retains some, substantially all, or all of the therapeutic or biological activity of the protein. In some embodiments, the protein is one that, if not expressed or produced or if substantially reduced in expression or production, would give rise to a disease. Preferably, the protein is derived or obtained from a mammal.

In various embodiments of the invention, when the physiologically active protein conjugated to a physiologically acceptable polymer is a protein or fragment thereof possessing a biological activity of the protein, the physiologically active protein has an amino acid sequence identical to the amino acid sequence to the corresponding portion of the unconjugated human or mammalian protein. In other embodiments, the physiologically active protein of the conjugate is a protein native to the species of the human or mammal. In other embodiments, the protein or fragment thereof, is substantially homologous (i.e., at least 80%, 85%, 90%, 95%, 96%, 97%, 98%, or 99% identical in amino acid sequence over a length of at least 10, 25, 50, 100, 150, or 200 amino acids, or the entire length of the active agent) to a native sequence of the corresponding human or mammalian protein.

Methods of Making a Protein

Methods for making recombinant proteins are well-known in the art. Methods of producing cells, including mammalian cells, which express DNA or RNA encoding a recombinant protein are described in U.S. Pat. Nos. 6,048,729, 5,994,129, and 6,063,630. The teachings of each of these applications are incorporated herein by reference in their entirety.

In one embodiment, a nucleic acid construct used to express a polypeptide or fragment, or analog thereof is one which is expressed extrachromosomally (episomally) in the transfected mammalian cell or one which integrates, either randomly or at a pre-selected targeted site through homologous recombination, into the recipient cell's genome. A construct which is expressed extrachromosomally comprises, in addition to polypeptide-encoding sequences, sequences sufficient for expression of the protein in the cells and, optionally, for replication of the construct. It typically includes a promoter, a polypeptide-encoding DNA sequence and a polyadenylation site. The DNA encoding the protein is positioned in the construct in such a manner that its expression is under the control of the promoter. Optionally, the construct may contain additional components such as one or more of the following: a splice site, an enhancer sequence, a selectable marker gene under the control of an appropriate promoter, and an amplifiable marker gene under the control of an appropriate promoter.

In those embodiments in which the DNA construct integrates into the cell's genome, it includes the polypeptide-encoding nucleic acid sequences. Optionally, it can include a promoter and an enhancer sequence, a polyadenylation site or sites, a splice site or sites, nucleic acid sequences which encode a selectable marker or markers, nucleic acid sequences which encode an amplifiable marker and/or DNA homologous to genomic DNA in the recipient cell to target integration of the DNA to a selected site in the genome (targeting DNA or DNA sequences).

Host Cells

Host cells used to produce recombinant proteins are bacterial, yeast, insect, non-mammalian vertebrate, or mammalian cells; the mammalian cells include, but are not limited to, hamster, monkey, chimpanzee, dog, cat, bovine, porcine, mouse, rat, rabbit, sheep and human cells. The host cells include immortalized cells (a cell line) or non-immortalized (primary or secondary) cells and include any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), muscle cells, hepatocytes and precursors of these somatic cell types.

Commonly used host cells include prokaryotic cells such as gram negative or gram positive bacteria, i.e., any strain of *E. coli, Bacillus, Streptomyces, Saccharomyces, Salmonella*, and the like; eukaryotic cells such as CHO (Chinese hamster ovary) cells; baby hamster kidney (BHK) cells; human kidney 293 cells; COS-7 cells; insect cells such as D. Mel-2, Sf4, Sf5, Sf9, and Sf21 and High 5; plant cells and various yeast cells such as *Saccharomyces* and *Pichia*.

Host cells containing the polypeptide-encoding DNA or RNA are cultured under conditions appropriate for growth of the cells and expression of the DNA or RNA. Those cells which express the polypeptide are identified, using known methods, and the recombinant protein isolated and purified, using known methods; either with or without amplification of polypeptide production. Identification is carried out, for example and without limitation, through screening genetically modified mammalian cells displaying a phenotype indicative of the presence of DNA or RNA encoding the protein, such as PCR screening, screening by Southern blot analysis, or screening for the expression of the protein. Selection of cells having incorporated protein-encoding DNA may be accomplished by including a selectable marker in the DNA construct and culturing transfected or infected cells containing a selectable marker gene under conditions appropriate for survival of only those cells that express the selectable marker gene. Further amplification of the introduced DNA construct is affected, in certain aspects, by culturing genetically modified cells under conditions appropriate for amplification (e.g., culturing genetically modified cells containing an amplifiable marker gene in the presence of a concentration of a drug at which only cells containing multiple copies of the amplifiable marker gene can survive).

In one example of the present invention, the protein is a physiologically active protein, protein complex or polypeptide, particularly a therapeutic protein, or a biologically active derivative thereof. As used herein, the term "biologically active derivative" includes any derivative of a protein, protein complex or polypeptide having substantially the same functional and/or biological properties of said protein, protein complex or polypeptide, such as binding properties, and/or the same structural basis, such as a peptidic backbone or a basic polymeric unit.

Recombinant proteins which are physiologically active proteins or therapeutic proteins include, but are not limited to, cytokines, growth factors, therapeutic coagulation proteins or blood clotting factors, enzymes, chemokines, soluble cell-surface receptors, cell adhesion molecules, antibodies, hormones, cytoskeletal proteins, matrix proteins, chaperone proteins, structural proteins, metabolic proteins, and other therapeutic proteins known to those of skill in the art. Exemplary recombinant proteins which are used as therapeutics include, but are not limited to, Factor VIII, Factor VIII:C, Antihemophilic Factor, Factor VII, Factor IX and von Willebrand factor, erythropoietin, interferons, insulin, CTLA4-Ig, alpha-glucocerebrosidase, alpha-glucosidase, follicle stimulating hormone, anti-CD20 antibody, anti-HER2 antibody, anti-CD52 antibody, TNF receptor, and others known in the art. See, for example, Physicians Desk Reference, $62^{nd}$ Edition, 2008, Thomson Healthcare, Montvale, N.J.

In one embodiment, the protein is a therapeutic coagulation factor or blood (clotting) factor, including but not limited to, Factor II, Factor V, Factor VII, Factor VIII, Factor IX, Factor X, Factor XI, Factor XII, Factor XIII, von Willebrand Factor, protein C, antithrombin III, and activated forms of any one of these proteins. In a related embodiment, the protein complex comprises one or more blood factors. Exemplary protein complexes of blood factos include a complex between FVIII and VWF.

Blood Factors

In one specific example of the present invention, the protein is a plasma-derived (plasmatic) and/or recombinant von Willebrand factor (VWF) or a biologically active derivative thereof. The term "plasma-derived VWF (pVWF)" includes mature VWF obtained from a mammal. One biologically active derivative of said pVWF is pro-VWF which contains the pro-peptide. In one example of the present invention the protein is selected from the group consisting of immature VWF including the precursor VWF molecule (pre-pro-VWF) synthesized by endothelial cells and megakaryocytes, the VWF propeptide (pro-VWF), and mature plasma-derived VWF obtained upon cleavage of the signal peptide and pro-peptide, respectively, of the precursor molecule. Further examples of biologically active derivatives of plasmatic VWF include pro-drugs which are processed or converted into the biologically active form, or are biologically active as such, truncated forms, forms having deletions, forms having substitutions, forms having additions other than pro-forms, fragments of the mature form, chimeric forms, and forms having post-translational modifications as compared to the natural form. The term "recombinant VWF (rVWF)" includes VWF obtained via recombinant DNA technology having optionally a glycosylation pattern which is pharmacologically acceptable. Specific examples thereof include VWF without A2 domain thus resistant to proteolysis (Lankhof et al., Thromb Haemost.; 77:1008-1013, 1997) and the VWF fragment from Val 449 to Asn 730 including the glycoprotein Ib-binding domain and binding sites for collagen and heparin (Pietu et al., Biochem Biophys Res Commun.; 164:1339-1347, 1989).

von Willebrand Factor exists in plasma in a series of multimer forms of a molecular weight of from $1 \times 10^6$ to $20 \times 10^6$ Dalton. VWF (Genbank Accession No. NP_000543) is a glycoprotein primarily formed in the endothelial cells of mammals and subsequently secreted into circulation. In this connection, starting from a polypeptide chain having a molecular weight of approximately 220 kD, a VWF dimer having a molecular weight of 550 kD is produced in the cells by the formation of several sulfur bonds. Further polymers of the VWF with increasing molecular weights, up to 20 million Dalton, are formed by the linking of VWF dimers. It is presumed that particularly the high-molecular VWF multimers have an essential importance in blood coagulation.

VWF syndrome manifests clinically when there is either an underproduction or an overproduction of VWF. Overproduction of VWF causes increased thrombosis (formation of a clot or thrombus inside a blood vessel, obstructing the flow of blood) while reduced levels of, or lack of, high-molecular forms of VWF causes increased bleeding and an increased bleeding time due to inhibition of platelet aggregation and wound closure.

A VWF deficiency may also cause a phenotypic hemophilia A since VWF is an essential component of functional Factor VIII. In these instances, the half-life of Factor VIII is reduced to such an extent that its function in the blood coagulation cascade is impaired. Patients suffering from von Willebrand disease (VWD) or VWF syndrome frequently exhibit a Factor VIII deficiency. In these patients, the reduced Factor VIII activity is not the consequence of a defect of the X chromosomal gene, but an indirect consequence of the quantitative and qualitative change of VWF in plasma. The differentiation between hemophilia A and vWD may normally be effected by measuring the VWF antigen or by determining the ristocetin-cofactor activity. Both the VWF antigen content and the ristocetin cofactor activity are lowered in most vWD patients, whereas they are normal in hemophilia A patients. VWF products for the treatment of VWF syndrome include, but are not limited to: HUMATE-P; and, IMMUNATE®, INNOBRAND®, and 8Y®, which therapies comprising FVIII/VWF concentrate from plasma.

In a related embodiment, the protein is Factor VIII. Factor VIII (FVIII) is a blood plasma glycoprotein of about 260 kDa molecular mass produced in the liver of mammals (Genbank Accession No. NP_000123). It is a critical component of the cascade of coagulation reactions that lead to blood clotting. Within this cascade is a step in which Factor IXa, in conjunction with FVIII, converts Factor X (Genbank Accession No. NP_000495) to an activated form, Factor Xa. FVIII acts as a cofactor at this step, being required with calcium ions and phospholipid for the activity of Factor IXa. The two most common hemophilic disorders are caused by a deficiency of functional FVIII (Hemophilia A, about 80% of all cases) or functional Factor IXa (Hemophilia B or Christmas Factor disease). FVIII circulates, in plasma at a very low concentration and is bound non-covalently to von Willebrand Factor (VWF). During hemostasis, FVIII is separated from VWF and acts as a cofactor for activated Factor IX (FIXa)-mediated Factor X (FX) activation by enhancing the rate of activation in the presence of calcium and phospholipids or cellular membranes.

FVIII is synthesized as a single-chain precursor of approximately 270-330 kD with the domain structure A1-A2-B-A3-$C_1$-$C_2$. When purified from plasma, FVIII is composed of a heavy chain (A1-A2-B) and a light chain (A3-C1-C2). The molecular mass of the light chain is 80 kD whereas, due to proteolysis within the B domain, the heavy chain is in the range of 90-220 kD.

FVIII is also synthesized as a recombinant protein for therapeutic use in bleeding disorders. Various in vitro assays have been devised to determine the potential efficacy of recombinant FVIII (rFVIII) as a therapeutic medicine. These assays mimic the in vivo effects of endogenous FVIII. In vitro thrombin treatment of rFVIII results in a rapid increase and subsequent decrease in its procoagulant activity, as measured by in vitro assay. This activation and inactivation coincides with specific limited proteolysis both in the heavy and the light chains, which alter the availability of different binding epitopes in FVIII, e.g., allowing FVIII to dissociate from VWF and bind to a phospholipid surface or altering the binding ability to certain monoclonal antibodies.

Until recently, the standard treatment of Hemophilia A involved frequent infusion of preparations of FVIII concentrates derived from the plasmas of human donors. While this replacement therapy is generally effective, such treatment puts patients at risk for virus-transmissible diseases such as hepatitis and AIDS. Although this risk has been reduced by further purification of FVIII from plasma by immunopurification using monoclonal antibodies, and by inactivating viruses by treatment with either an organic solvent or heat, such preparations have greatly increased the cost of treatment and are not without risk. For these reasons, patients have been treated episodically, rather than prophylactically. A further complication is that about 15% of patients develop inhibitory antibodies to plasma-derived FVIII. Patients with severe haemophilia A with FVIII levels below 1%, are generally on prophylactic therapy with the aim of keeping FVIII above 1% between doses. Taking into account the average half-lives of the various FVIII products in the circulation, this can usually be achieved by giving FVIII two to three times a week.

An important advance in the treatment of Hemophilia A was the isolation of cDNA clones encoding the complete 2,351 amino acid sequence of human FVIII (see, Wood et al, Nature, 312: 330 (1984) and U.S. Pat. No. 4,757,006) and the provision of the human FVIII gene DNA sequence and recombinant methods for its production. FVIII products for the treatment of hemophilia include, but are not limited to: ADVATE® (Antihemophilic Factor (Recombinant), Plasma/Albumin-Free Method, rAHF-PFM), recombinant Antihemophilic Factor (BIOCLATE™, GENARC®, HELIXATE FS®, KOATE®, KOGENATE FS®, RECOMBINATE®): MONOCLATE-P®, purified preparation of Factor VIII:C, Antihemophilic Factor/von Willebrand Factor Complex (Human) HUMATE-P® and ALPHANATE®, Anti-hemophilic Factor/von Willebrand Factor Complex (Human); and HYATE C®, purified pig Factor VIII. ADVATE®, is produced in CHO-cells and manufactured by Baxter Healthcare Corporation. No human or animal plasma proteins or albumin are added in the cell culture process, purification, or final formulation of ADVATE®.

Factor VII (proconvertin), a serine protease enzyme, is one of the central proteins in the blood coagulation cascade (Genbank Accession No. NP_000122). The main role of Factor VII (FVII) is to initiate the process of coagulation in conjunction with tissue factor (TF). Upon vessel injury, TF is exposed to the blood and circulating Factor VII. Once bound to TF, FVII is activated to FVIIa by different proteases, among which are thrombin (Factor Ia), activated Factor X and the FVIIa-TF complex itself. Recombinant human Factor VIIa (NOVOSEVEN®) has been introduced for use in uncontrollable bleeding in hemophilia patients who have developed inhibitors against replacement coagulation factor.

Factor IX (FIX, Christmas Factor) (Genbank Accession No. NP_000124) is a serine protease that is inactive unless activated by Factor XIa or Factor VIIa (of the tissue factor pathway). When activated into Factor IXa, it acts by hydrolyzing an arginine-isoleucine bond in Factor X to form Factor Xa. Factor VIII is a required cofactor for FIX protease activity (Lowe G D, Br. J. Haematol. 115: 507-13, 2002). Deficiency of Factor IX causes hemophilia B or Christmas disease.

Additional blood factors include Factor II (thrombin) (Genbank Accession No. NP_000497), deficiencies of which cause thrombosis and dysprothrombinemia; Factor V, (Genbank Accession No. NP_000121), deficiencies of which cause hemorrhagic diathesis or a form of thrombophilia, which is known as activated protein C resistance, Factor XI (Genbank Accession No. NP_000119), deficiencies of which cause Rosenthal's syndrome (hemophilia C), and Factor XIII subunit A (Genbank Accession No. NP_000120) and subunit B (Genbank Accession No. NP_001985), deficiencies of which are characterized as a type I deficiency (deficiency in both the A and B subunits) and type II deficiency (deficiency in the A subunit alone), either of which can result in a lifelong bleeding tendency, defective wound healing, and habitual abortion; Factor XII (Genbank Accession No. NP_000496); protein C (Genbank Accession No. NP_000303); antithrombin III (Genbank Accession No. NP_000479), and activated forms thereof.

Polypeptide Variants and Analogs

Methods of the invention are useful to rapidly detect recombinant proteins in a sample, as well as fragments, analogs or variants of the recombinant protein, and further may be useful to detect naturally-occurring protein which may exist as fragments or allelic variants in vivo wherein glycosylation differences aredetected.

Methods for preparing polypeptide fragments, analogs or variants are well-known in the art. Fragments of a polypeptide are prepared using methods well known in the art, including enzymatic cleavage (e.g., trypsin, chymotrypsin) and also using recombinant means to generate a polypeptide fragment having a specific amino acid sequence. Fragments may be generated to comprise a ligand-binding domain, a receptor-binding domain, a dimerization or multimerization domain, or any other identifiable domain known in the art.

Methods of making polypeptide analogs are also well-known. Analogs are, in certain aspects, substantially homologous or substantially identical to the naturally-occurring polypeptide from which the analog is derived, and analogs contemplated by the invention are those which retain at least some of the biological activity of the naturally-occurring polypeptide.

Substitution analogs typically exchange one amino acid of the wild-type for another at one or more sites within the protein, and are, in certain aspects, designed to modulate one or more properties of the polypeptide, such as stability against proteolytic cleavage, without the loss of other functions or properties. Substitutions of this kind are generally conservative. By "conservative amino acid substitution" is meant substitution of an amino acid with an amino acid having a side chain of a similar chemical character. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine).

Polynucleotide analogs and fragments may be readily generated by a worker of skill to encode biologically active fragments, variants, or mutants of the naturally occurring molecule that possess the same or similar biological activity to the naturally occurring molecule. Routinely practiced methods include PCR techniques, enzymatic digestion of DNA encoding the protein molecule and ligation to heterologous polynucleotide sequences, and the like. For example, point mutagenesis, using PCR and other techniques well-known in the art, may be employed to identify with particularity which amino acid residues are important in particular activities associated with protein activity. Thus, one of skill in the art will be able to generate single base changes in the DNA strand to result in an altered codon and a missense mutation.

It is further contemplated that the protein or polypeptide is modified to make an analog which is a fusion protein comprising a second agent which is a polypeptide. In one embodiment, the second agent which is a polypeptide is an enzyme, a growth factor, a cytokine, a chemokine, a cell-surface receptor, the extracellular domain of a cell surface receptor, a cell adhesion molecule, or fragment or active domain of a protein described above or of any other type of protein known in the art. In a related embodiment, the second agent is a blood clotting factor such as Factor II, Factor V, Factor VII, Factor VIII, Factor IX, Factor X, Factor XI, Factor XII, Factor XIII, von Willebrand Factor, protein C, antithrombin III, and activated forms thereof. The fusion protein contemplated is made by chemical or recombinant techniques well-known in the art.

Protein variants contemplated include polypeptides chemically modified by such techniques as ubiquitination, glycosylation, conjugation to therapeutic or diagnostic agents, labeling (e.g., with radionuclides or various enzymes), covalent polymer attachment such as PEGylation (derivatization with polyethylene glycol), introduction of non-hydrolyzable bonds, and insertion or substitution by chemical synthesis of amino acids such as ornithine, which do not normally occur in human proteins. Variants retain the binding properties of non-modified molecules of the invention.

Additional polypeptide variants useful in the methods of the present invention include polypeptides comprising polysialylate (PSA) moieties. Methods for preparing polysialylated polypeptide are described in U.S. Patent Publication 20060160948 and Saenko et al., Haemophilia 12:42-51, 2006.

Physiologically Acceptable Polymers

In one embodiment, the invention contemplates chemically modified proteins or polypeptides, which have been linked to a chemical moiety that provides advantageous effects to production, viability of the protein or polypeptide. For example, nonspecific or site-specific conjugation of physiologically acceptable polymers to polypeptides is known in the art to improve half-life by potentially reducing immunogenicity, renal clearance, and/or improving protease resistance.

A physiologically acceptable polymer molecule includes polymer molecules which, for example, are substantially soluble in an aqueous solution or may be present in form of a suspension and have substantially no negative impact, such as side effects, to mammals upon administration of a polymer molecule-protein-conjugate in a pharmaceutically effective amount and are regarded as biocompatible. There is no particular limitation to the physiologically acceptable polymer molecule used according to the present invention.

The polymer molecules are typically characterized as having for example from about 2 to about 1000, or from about 2 to about 300 repeating units. Examples of such polymer molecules include, but are not limited to, poly(alkylene glycols) such as polyethylene glycol (PEG), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol), polyphosphaszhene, polyoxazoline, poly(N-acryloylmorpholine), poly(alkylene oxide) polymers, poly(maleic acid), poly(DL-alanine), polysaccharides, such as carboxymethylcellulose, dextran, hyaluronic acid and chitin, poly(meth)acrylates, and combinations of any of the foregoing.

For example water-soluble polymers, including but not limited to, poly(ethylene glycol) (PEG), poly(ethylene oxide) (PEO), polyoxyethylene (POE), polyvinyl alcohols, hydroxyethyl celluloses, or dextrans, are commonly conjugated to proteins or peptides to increase stability or size, etc., of a protein or peptide.

PEG, PEO or POE refers to an oligomer or polymer of ethylene oxide. PEGs and PEOs include molecules with a distribution of molecular weights, i.e., polydisperse. The size distribution is characterized statistically by its weight average molecular weight (Mw) and its number average molecular weight (Mn), the ratio of which is called the polydispersity index (Mw/Mn). Mw and Mn are measured, in certain aspects, by mass spectroscopy. Most of the PEG-protein conjugates, particularly those conjugated to PEG larger than 1 KD, exhibit a range of molecular weights due to a polydisperse nature of the parent PEG molecule. For example, in case of mPEG2K (Sunbright ME-020HS, NOF), actual molecular masses are distributed over a range of 1.5~3.0 KD with a polydispersity index of 1.036. Exceptions are proteins conjugated to MS (PEG)n (N=4, 8, 12 or 24, e.g., PEO4, PEO12)-based reagents (Pierce), which are specially prepared as monodisperse mixtures with discrete chain length and defined molecular weight.

The physiologically acceptable polymer molecule is not limited to a particular structure and is, in various aspects, linear (e.g. alkoxy PEG or bifunctional PEG), branched or multi-armed (e.g. forked PEG or PEG attached to a polyol core), dentritic, or with degradable linkages. Moreover, the internal structure of the polymer molecule is organized in any number of different patterns and is selected from the group consisting of homopolymer, alternating copolymer, random copolymer, block copolymer, alternating tripolymer, random tripolymer, and block tripolymer.

In one specific example of the present invention, the physiologically acceptable polymer molecule is PEG and derivatives thereof. There is no specific limitation of the PEG used according to the present invention. For example, PEG-protein conjugates include but are not limited to linear or branched conjugates, polymer:proteins conjugated by NUS (N-hydroxysuccinimide)- or aldehyde-based chemistry, variants with a different chemical linkage between the PEG chain and conjugation site, and variants differing in lengths. The average molecular weight of the PEG will range from about 3 kiloDalton ("kDa") to about 200 kDa, from about 5 to about 120 kDa, from about 10 to about 100 kDa, from about 20 to about 50 kDa, from about 5 kDa to about 60 kDa, from about 5 kDa to about 40 kDa, from about 3 to about 30 kDa, from about 5 kDa to about 25 kDa, from about 5 kDa to about 15 kDa, or from about 5 kDa to about 10 kDa. In certain embodiments, the PEG is about 5 kDa, about 10 kDa, about 15 kDa, about 20 kDa, about 25 kDa, is about 30 kDa, about 35 kDa, about 40kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa, about 100 kDa, about 110 kDa, about 120 kDa, about 130 kDa, about 140 kDa, about 150 kDa, about 160 kDa, about 170 kDa, about 180 kDa, about 190 kDa, or about 200 kDa.

The invention contemplates PEG-protein conjugates selected from the group consisting of linear PEG-protein conjugates that are NHS-conjugated and range in length from —(CH2-CH2-O)n-, where n=1 to 2000, linear PEG-protein conjugates that are aldehyde-conjugated and range in length from —(CH2-CH2-O)n-, where n=1 to 2000, two-arm branched PEG-protein conjugates that are NHS-conjugated and range in length, from 3 to 100 kDa in mass, and three-arm branched PEG-protein conjugates that are NHS-conjugated. The invention also contemplates PEG-protein conjugates that contain different chemical linkages (—CO(CH2)n-, and —(CH2)n- where n=1 to 5) between its conjugation site and the PEG chain. The invention further contemplates charged, anionic PEG-protein conjugates to reduce renal clearance, including but not limited to carboxylated, sulfated and phosphorylated compounds (anionic) (Caliceti & Veronese, Adv Drug Deliv Rev 2003 55(10):1261-77; Perlman et al., J Clin Endo Metab 2003 88(7):3227-35; Pitkin et al., Antimicrob Agents Chemother 1986 29(3): 440-44; Vehaskari et al., Kidney Intl 1982 22 127-135). In a further embodiment, the peptide is optionally conjugated to a moiety including a bisphosphonate, a water-soluble polymer such as PEG or PEO, carbohydrates, fatty acids, or further amino acids.

Macromolecule chemical modification is, in one aspect, performed in a non-specific fashion (leading to mixtures of modified species) or in a site-specific fashion (based on wild-type macromolecule reactivity-directed modification and/or site-selective modification using a combination of site-directed mutagenesis and chemical modification) or, alternatively, using expressed protein ligation methods (Curr Opin Biotechnol. 13(4):297-303 (2002)).

To discover if the in vivo therapeutic half-life of a peptide would benefit from PEGylation, a variety of different PEG-protein conjugates are synthesized, characterized in vitro and in-vivo for pharmacokinetics. In order to both optimize the potential effects of PEGylation a design strategy is employed wherein polymer length, conformation, and charge of PEG is varied.

Methods for preparing the PEGylated protein of the present invention generally comprise the steps of (a) reacting the protein of interest with polyethylene glycol under conditions whereby PEG becomes attached to the N-terminus/C-terminus of the protein, and (b) obtaining the reaction product(s). Because PEGylating a protein might significantly alter the intrinsic activity of the protein, different types of PEG are explored. The chemistry used for PEGylation of protein includes, but is not limited to, the acylation of the primary amines of the protein using the NHS-ester of methoxy-PEG (O—[(N-Succinimidyloxycarbonyl)-methyl]-O'-methylpolyethylene glycol). Acylation with methoxy-PEG-NHS or methoxy-PEG-SPA results in an amide linkage that eliminates the charge from the original primary amine (also, Boc-PEG for C-terminus). Unlike ribosome protein synthesis, synthetic peptide synthesis proceeds from the C-terminus to the N-terminus. Therefore, Boc-PEG is one method (i.e. using tert-(B)utyl (O)xy (c)arbonyl (Boc, t-Boc) synthesis) to attach PEG to the C-terminus of the peptide (R. B. Merrifield (1963). "Solid Phase Peptide Synthesis. I. The Synthesis of a Tetrapeptide". J. Am. Chem. Soc. 85 (14): 2149-2154). (F)luorenyl-(m)eth(O)xy-(c)arbonyl (FMOC) chemistry (Atherton, E.; Sheppard, R.C. (1989). *Solid Phase peptide synthesis: a practical approach*. Oxford, England: IRL Press.) is favored because it does not require the hazardous use of hydrofluoric acid to remove side-chain protecting groups. The present methods provide for a substantially homogenous mixture of polymer:protein conjugate. "Substantially homogenous" as used herein means that only polymer:protein conjugate molecules are observed. The polymer: protein conjugate has biological activity and the present "substantially homogenous" PEGylated protein preparations are those which are homogenous enough to display the advantages of a homogenous preparation, e.g., ease in clinical application in predictability of lot to lot pharmacokinetics.

Exemplary stable linkers that can facilitate conjugation of the physiologically acceptable polymer to the polypeptide of interest include, but are not limited to, amide, amine, ether, carbamate, thiourea, urea, thiocarbamate, thiocarbonate, thioether, thioester, and dithiocarbamate linkages, such as ω,ω-aminoalkane, N-carboxyalkylmaleimide, or aminoalkanoic acids, maleimidobenzoyl sulfosuccinimide ester, glutaraldehyde, or succinic anhydride, N-carboxymethylmaleimide N,N'-disuccinimidyl oxalate and 1,1'-bis[6-(trifluoromethy)benzo-triazolyl]oxalate.

In other embodiments, the physiologically acceptable polymer is conjugated to the polypeptide using a releasable linker. In one embodiment, the releasable linker is a hydrolyzable linkers A hydrolyzable or degradable bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Methods of making conjugates comprising water soluble polymers having hydrolyzable linkers are described in U.S. Pat. No. 7,259,224 (Nektar Therapeutics) and U.S. Pat. No. 7,267,941 (Nektar Therapeutics and National Institutes of Health). For example, a PEG can be prepared having ester linkages in the polymer backbone that are subject to hydrolysis. This hydrolysis results in cleavage of the polymer into fragments of lower molecular weight. Appropriate hydrolytically unstable or weak linkages include but are not limited to carboxylate ester, phosphate ester, anhydrides, acetals, ketals, acyloxyalkyl ether, imines, orthoesters, peptides and oligonucleotides, thioesters, thiolesters, and carbonates. Hydrolytically degradable linkages that may be contained within the polymer backbone include carbamate, carbonate, sulfate, and acyloxyalkyl ether linkages; imine linkages, resulting, for example, from reaction of an amine and an aldehyde (see, e.g., Ouchi et al., Polymer Preprints, 38(1):582-3 (1997)); carbamate, phosphate ester, hydrazone, acetal, ketal, or orthoester linkages, including acetone-bis-(N-maleimidoethyl)ketal linkers (MK).

In a further embodiment, the polymer molecules contemplated for use in the PEGylation approaches described herein are selected from among water-soluble polymers or a mixture thereof. The polymer may have a single reactive group, such as an active ester for acylation or an aldehyde for alkylation, so that the degree of polymerization may be controlled. The water-soluble polymer, or mixture thereof if desired, may be selected from the group consisting of, for example, PEG, monomethoxy-PEG, PEO, dextran, poly-(N-vinyl pyrrolidone), propylene glycol homopolymers, fatty acids, a polypropylene oxide/ethylene oxide co-polymer, polyoxyethylated polyols (e.g., glycerol), HPMA, FLEXIMAR™, and polyvinyl alcohol, mono-(C1-C10)alkoxy-PEG, aryloxy-PEG, tresyl monomethoxy PEG, PEG propionaldehyde, bis-succinimidyl carbonate PEG, cellulose, other carbohydrate-based polymers, or mixtures thereof. In certain embodiments, the polymer selected is water-soluble so that the protein to which it is attached does not precipitate in an aqueous environment, such as a physiological environment. The polymer is, in various aspects, branched or unbranched. In one embodiment, for therapeutic use of the end-product preparation, the polymer is pharmaceutically acceptable. Methods for generating peptides comprising a PEG moiety are well-known in the art. See, for example, U.S. Pat. No. 5,824,784.

In one embodiment, the reactive aldehyde is PEG-propionaldehyde, which is water-stable, or mono-C1-C10 alkoxy or aryloxy derivatives thereof (see U.S. Pat. No. 5,252,714). As used herein, PEG is meant to encompass any of the forms of PEG that have been used to derivatize other proteins, such as mono-(C1-C10) alkoxy- or aryloxy-polyethylene glycol. In some embodiments, the polymer is branched or unbranched. In one embodiment, for therapeutic use of the end-product preparation, the polymer is pharmaceutically acceptable.

A protein bound to at least one physiologically acceptable polymer molecule includes a protein covalently bound or non-covalently bound by interactions such as ionic, hydrophobic, affinity, bioaffinity interactions, to one or more polymer molecules. In one embodiment, the polymer molecule is coupled to the protein by use of bifunctional reagents and via a spacer arm. In a related embodiment, the polymer molecule is coupled to the protein by affinity interaction. For example, the protein is biotinylated and avidin or streptavidin conjugated polymer molecules is bound to the protein. Further, polyclonal or monoclonal antibodies as well as fragments thereof are bound to a polymer molecule, and then this complex is bound to the protein. Polymer molecules are bound to the protein also by enzymatic methods such as, for example, the transfer of saccharides with polyglycosyltransferase (U.S. Pat. No. 6,379,933) or glycopegylation (US 2004 0132640). Another approach is the binding of polymer molecules to the protein on the basis of their biological function, like for example the binding of PEGylated collagens or collagen fragments to the A1 and A3 domains of the VWF protein. For this purpose, in certain aspects, collagens from type I and III, e.g. from human placenta, showing a strong interaction with the VWF are used. The binding of the polymer molecule is irreversible or reversible under physiological conditions after an in vivo-application of the protein.

In one example of the present invention, in step (a) the protein bound to at least one physiologically acceptable polymer molecule is immobilized on a substrate or carrier matrix, for example by an antibody being capable of specifically binding to said protein.

A substrate or carrier matrix does not have any specific limitations, and relates, for example, to an insoluble polymer material, which can be an organic polymer, such as polyamide or a vinyl polymer (e.g. poly(meth)acrylate, polystyrene and polyvinyl alcohol, or derivatives thereof), a natural polymer such as cellulose, dextrane, agarose, chitin and polyamino acids, or an inorganic polymer, such as glass or metallohydroxide. In certain embodiments, the substrate is in the form of a microcarrier, particles, membranes, strips, paper, film, pearls, beads or plates, such as microtiter plates. In one aspect, the protein bound to at least one physiologically acceptable polymer molecule is immobilized on the substrate directly by covalent coupling or via a carrier such as a linker molecule or an antibody immobilized on the substrate.

Detectable Labels

In some embodiments, the protein or polymer useful in the method of the invention is labeled to facilitate its detection. A "label" or a "detectable moiety" is a composition detectable by spectroscopic, photochemical, biochemical, immunochemical, chemical, or other physical means.

Depending on the screening assay employed, the protein or fragment thereof, or the polymer, or a portion thereof is labelled. The particular label or detectable group used is not a critical aspect of the invention, as long as it does not significantly interfere with the biological activity of the conjugate. The detectable group is any material having a detectable physical or chemical property. Thus, a label is any composition detectable by spectroscopic, photochemical, biochemical, immunochemical, electrical, optical or chemical means.

Examples of labels suitable for use in the present invention include, but are not limited to, fluorescent dyes (e.g., fluorescein isothiocyanate, Texas red, rhodamine, and the like), radiolabels (e.g., 3H, 125I, 35S, 14C, or 32P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. Preferably, the label in one embodiment is covalently bound to the biopolymer using an isocyanate reagent for conjugating an active agent according to the invention. In one aspect of the invention, the bifunctional isocyanate reagents of the invention are used to conjugate a label to a biopolymer to form a label biopolymer conjugate without an active agent attached thereto. The label biopolymer conjugate may be used as an intermediate for the synthesis of a labeled conjugate according to the invention or may be used to detect the biopolymer conjugate. As indicated above, a wide variety of labels are used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand binds to another molecules (e.g., streptavidin) molecule, which is either inherently detectable or covalently bound to a signal system, such as a detectable enzyme, a fluorescent compound, or a chemiluminescent compound.

In certain aspects, the conjugates are conjugated directly to signal generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labelling or signal producing systems that are used in the methods of the present invention, see U.S. Pat. No. 4,391,904.

Means for detecting labels are well known to those of skill in the art. Thus, for example, where the label is radioactive, means for detection include a scintillation counter (e.g., radioimmunoassay, scintillation proximity assay) (Pitas et al., Drug Metab Dispos. 34:906-12, 2006) or photographic film, as in autoradiography. Where the label is a fluorescent label, it may be detected by exciting the fluorochrome with the appropriate wavelength of light and detecting the resulting fluorescence (e.g., ELISA, immunoblot, flow cytometry, or other methods known in the art). The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art.

In one embodiment the label, the protein:polymer conjugate or the polymer:protein complex conjugate contemplated for use in the method are linked to a solid support, such as a substrate or carrier matrix, including but not limited to, a filter, a microcarrier, a particle, a membrane, a strip, paper, a film, a bead or a plate, or any other carrier matrix known in the art.

It is further contemplated that the labeled compounds may be labeled and interact in solution. For example, the capture antibody may be labeled with a fluorescent resonance energy transfer (FRET) donor molecule and the target molecule is labeled with a FRET acceptor molecule such that the molecules are in proximity when binding occurs. Alternatively, the target molecule may be labeled with the FRET donor and the antibody molecule the FRET acceptor. Another possibility is to separate quenching and fluorescent molecule both present on the antibody or target when target and antibody hybridize. The target molecule is only close enough for its label to emit if it is interacting with the reagent. This produces a system where the molecule only emits when it interacts with the reagent (direct monitoring). In one embodiment, a narrow band pass filter is used to block all wavelengths except that of the molecule's label. FRET molecule pairs are commercially available in the art (e.g., from Invitrogen, Carlsbad, Calif.), and may be used according to the manufacturer's protocol. FRET emissions are detected using optical imaging techniques, such as a CCD camera.

Another method of detecting antibody-antigen interactions is to label it with an electron donor. This donor label would give electrons to an electrical contact to which the reagent is bound. See, for example, Ghindilis, A. (Biochem Soc Trans. 28:84-9, 2000) and Dai et al. (Cancer Detect Prev. 29:233-40, 2005) which describe enzymes useful in and methods for electro immunoassays. The electron contact would then be read by an A to D (analog to digital) converter and quantified. The higher the electron count the more interactions took place.

One embodiment of a label capable of single molecule detection is the use of plasmon-resonant particles (PRPs) as optical reporters, as described in Schultz et al., *Proc. Nat'l Acad. Sci.*, 97:996-1001 (2000), incorporated herein by reference. PRPs are metallic nanoparticles, typically 40-100 nm in diameter, which scatter light elastically with remarkable efficiency because of a collective resonance of the conduction electrons in the metal (i.e., the surface plasmon resonance). The magnitude, peak wavelength, and spectral bandwidth of the plasmon resonance associated with a nanoparticle are dependent on the particle's size, shape, and material composition, as well as the local environment. By influencing these parameters during preparation, PRPs are formed that have scattering peak anywhere in the visible range of the spectrum. For spherical PRPs, both the peak scattering wavelength and scattering efficiency increase with larger radius, providing a means for producing differently colored labels. Populations of silver spheres, for example, are reproducibly prepared for which the peak scattering wavelength is within a few nanometers of the targeted wavelength, by adjusting the final radius of the spheres during preparation. Because PRPs are bright, yet nanosized, they are used as indicators for single-molecule detection; that is, the presence of a bound PRP in a field of view can indicate a single binding event.

It is contemplated that the assay and the detection are useful to determine the number of polymers bound to a protein or protein complex, or to determine the extent of free polymer in a solution, such as serum or plasma. The detectable signal observed in the method correlates with the number of polymers bound to the protein or protein complex, or free in solution when compared to a standard having a known amount of polymer.

Therefore, in one embodiment, the invention provides a method for determining the number of physiologically acceptable polymer molecules bound to a protein or a protein complex or free in solution comprising, contacting said polymer with an antibody that specifically binds said polymer, wherein the number of polymers bound by the antibody correlates with levels of antibody detected bound when compared to a known control.

In an alternate embodiment, the invention contemplates a method for determining the number of physiologically acceptable polymer molecules bound to a protein or a protein complex, contacting said protein or protein complex with an antibody that specifically binds said protein or protein complex, wherein the number of polymers bound by the antibody correlates with levels of antibody detected bound when compared to a known control.

In related embodiments, the method of the invention is carried out using an other detection regimens, for example, wherein the protein and polymer specific antibodies are used in any order as follows, wherein the first antibody listed is the antibody bound to the carrier matrix and the second antibody bound in the antibody that is detectable. Exemplary assays useful to detect the number of polymers bound to a protein or protein complex include an anti-polymer-anti-protein detection method, an anti-protein-anti-polymer detection method, or an anti-polymer-anti-polymer detection method, wherein the anti-polymer antibody is the same antibody for each binding step, or is a different polymer-specific antibody for each step. In a related embodiment, the assay is carried out using only an anti-polymer specific antibody or an anti-protein-specific antibody.

Kits

As an additional aspect, the invention includes kits which comprise one or more compounds or compositions packaged in a manner which facilitates their use to practice methods of the invention. In one embodiment, such a kit includes a composition comprising a protein or protein complex conjugated to a physiologically acceptable polymer, such as PEGylated Factor VIII, and an antibody or other molecule that specifically detects the water soluble polymer on the protein, packaged in a container such as a sealed bottle or vessel, with a label affixed to the container or included in the package that describes use of the compound or composition in practicing the method. In related embodiments, the binding agent is a soluble receptor, a ligand, a cofactor or another agent that specifically binds the protein, protein complex or polymer. The kit may optionally include reagents and buffers for preparation of the samples for detection of the polymer-protein complex. Preferably, the compound or composition is packaged in a unit dosage form. The kit may further include a device suitable for administering the composition according to a specific route of administration. Preferably, the kit contains a label that describes use of the modified blood factor composition.

In one embodiment of the present invention, the method includes an Enzyme Linked Immunosorbent Assay (ELISA) comprising the following steps:

(i) immobilizing an antibody being capable of specifically binding to a protein bound to at least one physiologically acceptable polymer molecule to an ELISA plate;

(ii) binding the protein of interest to the immobilized antibody; and (iii) detecting the amount of physiologically acceptable polymer molecule bound to the protein by an antibody being capable of specifically binding to a physiologically acceptable polymer molecule bound to said protein of interest.

The present invention will be further illustrated in the following examples, without any limitation thereto.

EXAMPLES

Example 1

Direct Enzyme Linked Immunosorbent Assay (ELISA) on the Antigen HSAP-2-SS (PEGylated Human Serum Albumin (hSA))

To determine if polyclonal antibodies to PEG generated using a PEGylated antigen injected into animals, human serum albumin (hSA) was linked to PEG and the protein conjugate injected into rabbits. The amount of anti-PEG antibody was then measured.

In brief, a polyclonal antibody is generated by immunization of rabbits (Richter A W et al. 1983; Int Arch Allergy Appl Immunol 70:124-31) with PEG covalently bound to human serum albumin (HSA). Rabbits are inoculated with preparations of the antigen HSAP-2-h-SS with about 380 µg/ml protein and a PEG concentration of 250 µg/ml. Serum samples of all animals are taken before the start and after 3 and 4 weeks and are subsequently tested for detectable antibody formation against the antigen HSAP-2-h-SS. The antigen HSAP-2-h-SS (PEGylated hSA) is coated in 0.1 M carbonate at pH 9.6 at 1 µg/ml. The samples are diluted in PBS-gelatin buffer and incubated with the wells and subsequently with a goat anti-rabbit IgG-HRP antibody using Single Incubation Multilayer Immune Technique (SIMIT) (Naser, W., J Immunol Methods. 129:151-7, 1990). In SIMIT, the ligand (e.g., antibodiy) and ligand binding agent (e.g., anti-antibody) are co-incubated in order that during a single incubation step, multiple layers of immunoreactants are formed thereby resulting in enhanced assay sensitivity. An antibody formation against the antigen HSAP-2-h-SS is detectable. The antigen can be coated directly on plate and there is an increase of titer with time of immunization FIG. 1A).

Figure 1B:
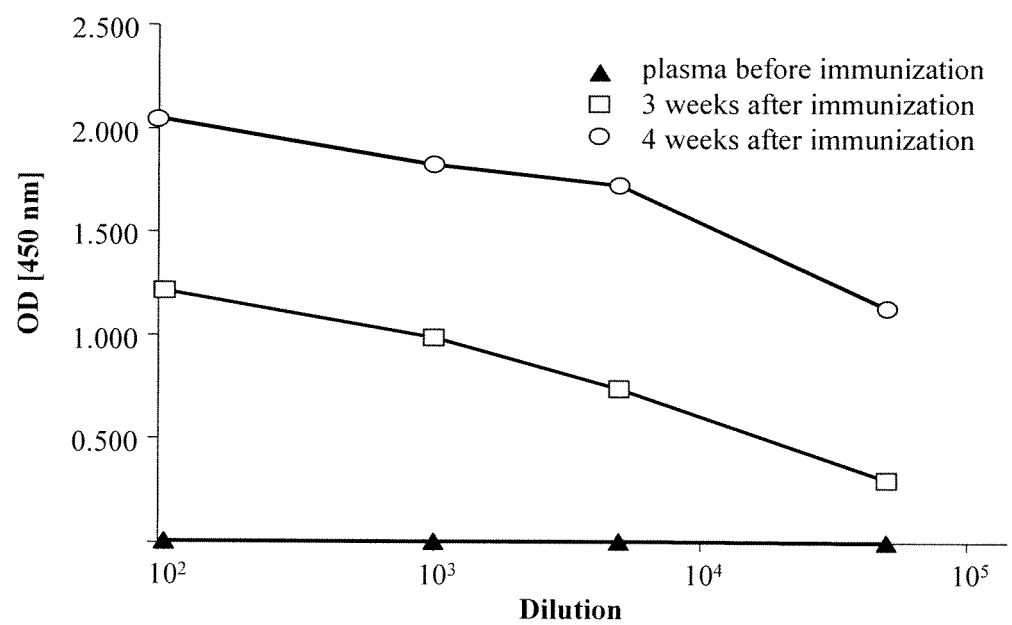

More specifically, PEGylated hSA was prepared according to Abuchowski et al (J Biol Chem 252: 3578-81, 1977). The PEGylated hSA had higher molecular weight as shown by high-performance size-exclusion chromatography and SDS-PAGE. Serum samples of all animals were taken before the start and after 3 and 4 weeks and pooled. These pooled samples were subsequently tested for antibody formation against the immunization antigen by a direct ELISA. Briefly, the PEGylated hSA was coated in 0.1 M sodium carbonate buffer, pH 9.6 at a concentration of 1 µg/mL to 96-well polystyrene microplates (Nunc Maxisorp F96). The pooled rabbit serum samples were diluted in phosphate-buffered saline (PBS) containing 1 mg/mL gelatin and incubated with the wells and subsequently with a goat anti-rabbit IgG-HRP antibody. An antibody formation against the immunization antigen was detectable. In addition, there was an increase of titer with time of immunization (FIG. 1B). The same method was used to measure the antibody titers in samples obtained in another immunization study. Table 1 shows the blank-corrected optical densities (OD) of samples taken at the start and after 36 and 50 days. Also in this case, the results for the sample dilutions 1/50 and 1/100 demonstrate the formation of IgG against the immunization antigen that increased with time.

TABLE 1

Anti-PEG IgG titers after immunization with PEGylated hSA

| Rabbit | Dilution 1/50 | | | Dilution 1/100 | | |
| --- | --- | --- | --- | --- | --- | --- |
|  | d0 | d36 | d50 | d0 | d36 | d50 |
| 1 | 0.000 | 0.699 | 0.651 | 0.000 | 0.480 | 0.260 |
| 2 | 0.000 | 0.420 | 0.329 | 0.000 | 0.233 | 0.116 |
| 3 | 0.000 | 0.162 | 0.084 | 0.000 | 0.098 | 0.022 |
| 4 | 0.000 | 0.440 | 0.343 | 0.000 | 0.212 | 0.116 |
| 5 | 0.000 | 0.423 | 0.408 | 0.000 | 0.196 | 0.115 |
| 6 | 0.003 | 0.152 | 0.115 | 0.002 | 0.114 | 0.079 |
| Mean | 0.001 | 0.383 | 0.322 | 0.000 | 0.222 | 0.118 |

These results show that a PEG conjugated hSA protein induces the production of polyclonal antibodies from subject animals.

Example 2

Inhibition of the Direct ELISA on the Antigen HSAP-2-SS by PEG

To determine if the binding of the anti-PEG antibody was specific for PEG, the ability of free PEG to interfere with antibody binding was assessed.

Figure 2A:
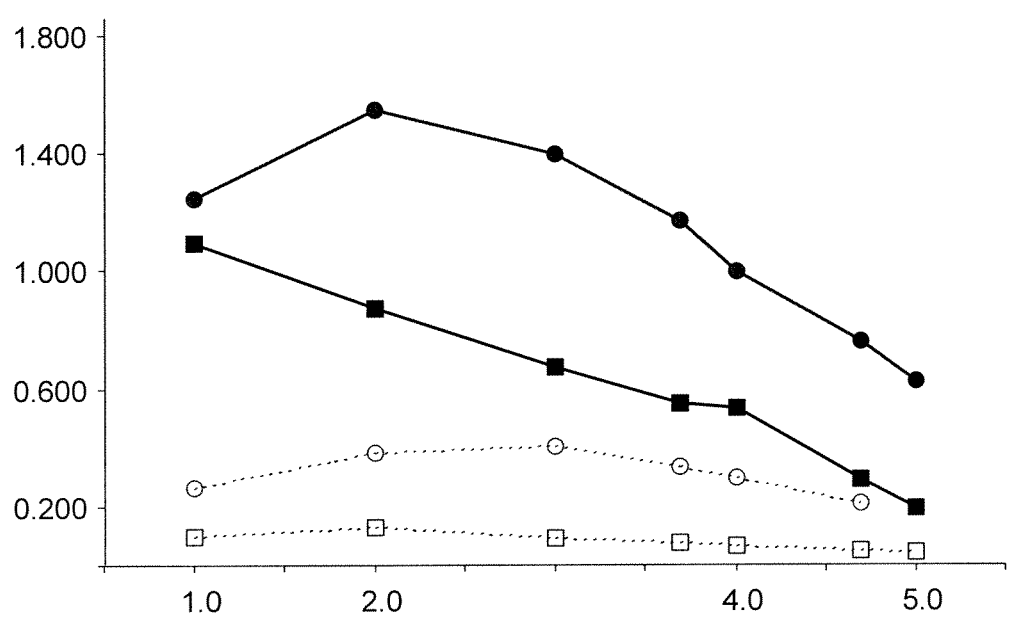
FIG. 2 shows the inhibition of the direct ELISA on the antigen HSAP-2-SS by PEG. Rabbits were immunized with the antigen HSAP-2-SS and serum samples are prepared as described in FIG. 1. The antigen HSAP-2-h-SS is coated on a surface in 0.1 M carbonate at pH 9.6 at 1 µg/ml. The samples were diluted in PBS-gelatin buffer or PBS-gelatin-1% PEG 5000 buffer (+1% PEG) and incubated with the wells and subsequently with a goat anti-rabbit IgG-HRP antibody (SIMIT). The optical density (OD) (vertical axis) is shown for the log dilution (horizontal axis) of the respective samples. □, 3 weeks+1% PEG; ■, 3 weeks; ○, 4 weeks+1% PEG; ●, 4 weeks.

In brief, rabbits are immunized with the antigen HSAP-2-SS and serum samples are prepared as described above (Example 1). The antigen HSAP-2-h-SS is coated on a surface in 0.1 M carbonate at pH 9.6 at 1 µg/ml. The samples are diluted in PBS-gelatin buffer or PBS-gelatin-1% PEG 5000 buffer (+1% PEG) and incubated with the wells and subsequently with a goat anti-rabbit IgG-HRP antibody (SIMIT). The binding of the antibody to the antigen (=PEGylated hSA) obtained by the immunization of rabbits can be inhibited by the addition of PEG 5000 to the sample dilution buffer (FIG. 2A).

Figure 2B:
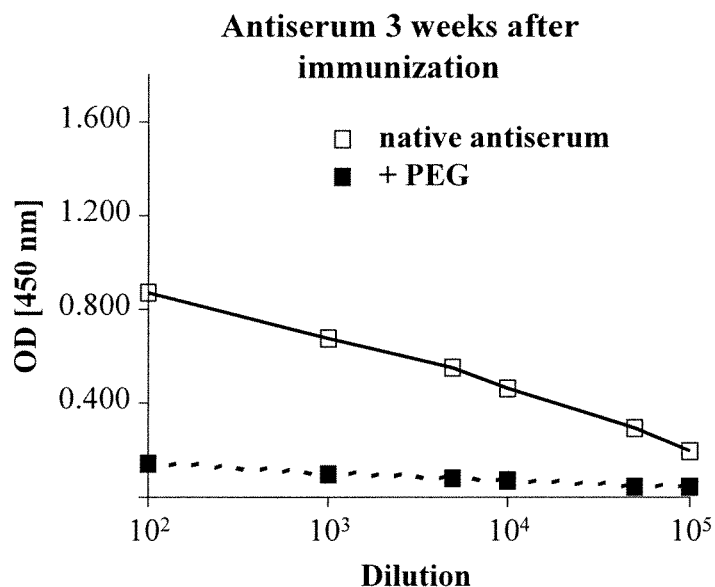
Figure 2C:
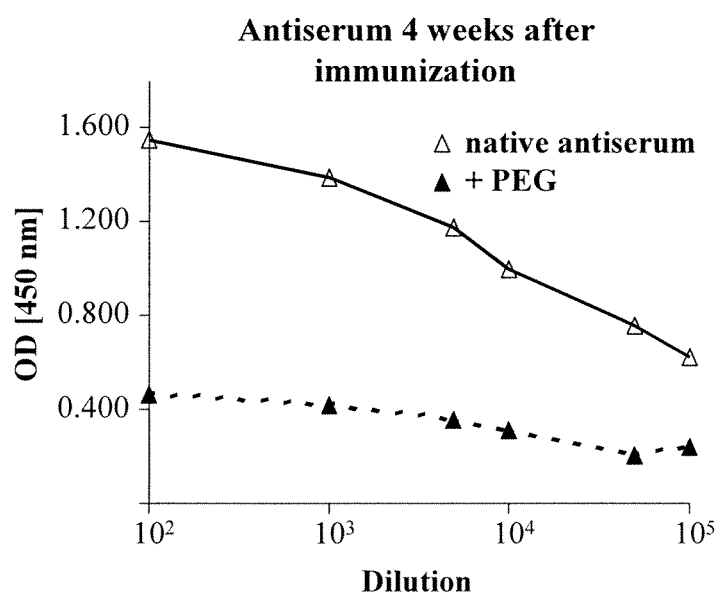

More specifically, the anti-PEG specificity of the antisera obtained by immunization with the PEGylated hSA was checked with an inhibition study. Plates (Example 1) were coated with the immunization antigen PEGylated hSA at a concentration of 10 µg/mL. Pooled rabbit serum samples taken 3 and 4 weeks after the start of the immunization were diluted in PBS-gelatin to obtain dilution series ranging from 1/100 to 1/100,000. PEG 5000 was added at a concentration of 10 mg/mL to inhibit the binding to PEGylated hSA. Bound rabbit IgG was detected by using a goat anti-rabbit IgG-peroxidase conjugate and the peroxidase substrate Sureblue. Polyethylene glycol (PEG) 5000 decreased the binding of rabbit IgG to the plate-immobilized PEGylated hSA (FIG. 2B)

These results demonstrate that the IgG contained in the rabbit serum specifically recognized and bound to PEG. Residual binding of rabbit IgG in the presence of PEG was caused by antibodies directed towards hSA. These non-PEG-specific IgGs were adsorbed by affinity chromatography on immobilized hSA.

Example 3

Direct ELISA on a PEG-Modified Plate

To determine if the anti-PEG antibody would bind PEG bound directly to the plastic, a direct PEG ELISA was developed.

Figure 3:
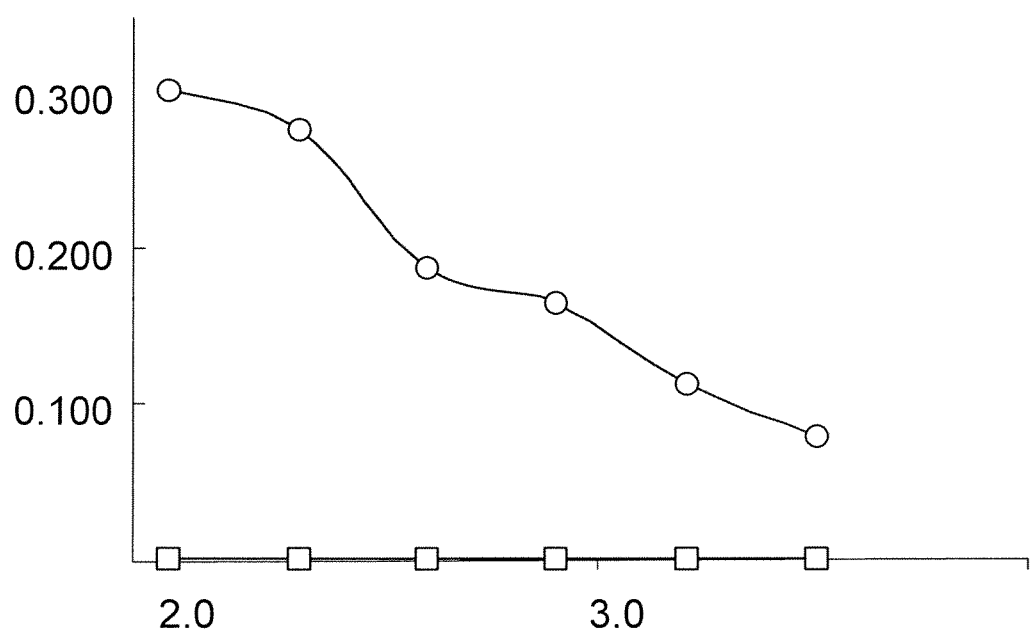
FIG. 3 shows the direct ELISA on a PEG-modified plate. Rabbits were immunized with the antigen HSAP-2-SS and serum samples are prepared as described in FIG. 1. A substrate (NUNC Maxisorp F96) is coated with mPEG-NPC 5000 at 1 mg/ml in 15 mM HEPES 2 hours at room temperature and then blocked with PBS-gelatin (5 mg/ml). The samples were diluted in PBS-gelatin buffer and incubated with the wells and subsequently with a goat anti-rabbit IgG-HRP antibody (SIMIT). The optical density (OD) (vertical axis) is shown for the log dilution (horizontal axis) of the respective samples. The optical density (OD) (vertical axis) is shown for the log dilution (horizontal axis) of the respective samples. ●, Pool 3 week; ■, Pool SPF (normal rabbit serum).

In brief, rabbits are immunized with the antigen HSAP-2-SS and serum samples are prepared as described above (Example 1). A substrate (NC Maxisorp F96) is coated with mPEG-NPC 5000 at 1 mg/ml in 15 mM HEPES 2 hours at room temperature and then blocked with PBS-gelatin (5 mg/ml). The samples are diluted in PBS-gelatin buffer and incubated with the wells and subsequently with a goat anti-rabbit IgG-HRP antibody (SIMIT). A binding of the antibodies present in the serum samples to a PEG-modified plate (NUNC Maxisorp F96) is detected (FIG. 3).

More specifically, rabbits were immunized with PEGylated hSA and serum samples were prepared as described above (Example 1). Plates (Example 1) were coated with mPEG-p-nitrophenyl carbonate (NPC; SunBio, Korea) 5000 at 1 mg/ml in 15 mM HEPES at room temperature for 2 hours and then blocked with PBS-gelatin (5 mg/ml). The serum samples were diluted with PBS-gelatin buffer, incubated with the wells and subsequently with a goat anti-rabbit IgG-peroxidase. A clear binding of IgG present in the rabbit serum samples to the PEG-modified plate was detected (FIG. 3). When the same procedure was carried out with polylysine- and $NH_2$-activated plates (Costar), no reaction could be observed.

These results demonstrate that the anti-PEG IgG contained in the rabbit serum samples recognized and bound to PEG.

Example 4

Direct ELISA on VWF and PEG-VWF To determine if the anti-PEG antibody will bind PEGylated proteins other than the immunization antigen, the anti-PEG antibodies were used in an ELISA with PEGylated von Willebrand Factor.

Figure 4A:
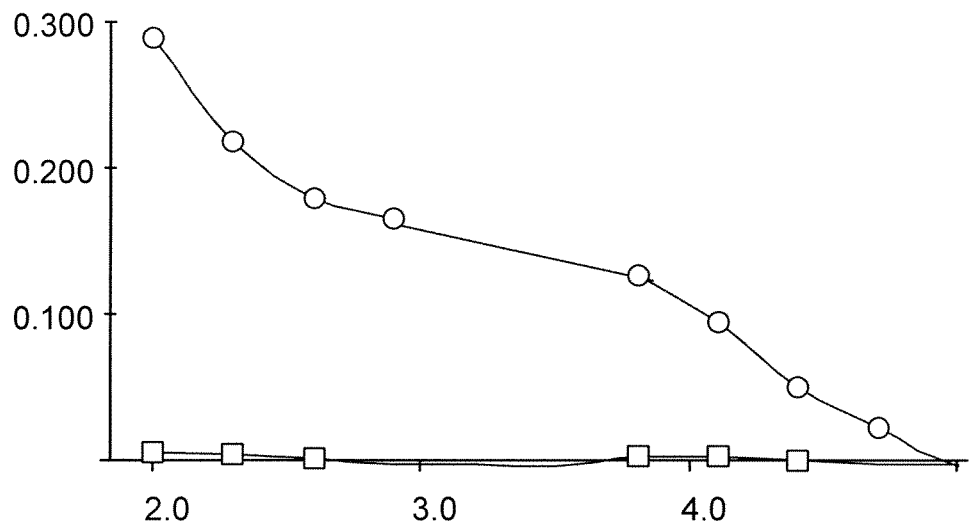
FIG. 4 shows the direct ELISA on VWF and PEG-VWF. Rabbits were immunized with the antigen HSAP-2-SS and serum samples are prepared as described FIG. 1. A substrate is coated with PEGylated VWF (PEG-VWF) in 0.1 M carbonate at pH 9.6, another substrate is coated with recombinant VWF (rVWF-12) in 0.1 M carbonate at pH 9.6. The samples were diluted in PBS-gelatin buffer and incubated with the wells and subsequently with a goat anti-rabbit IgG-HRP antibody (SIMIT). The optical density (OD) (vertical axis) is shown for the log dilution (horizontal axis) of the respective samples. ●, Pool 3 week (Coat: PEG-VWF); ■, Pool 3 week (Coat: rVWF-12).

In brief, rabbits are immunized with the antigen HSAP-2-SS and serum samples were prepared as described above (Example 1). A substrate is coated with PEGylated VWF (PEG-VWF) in 0.1 M carbonate at pH 9.6, another substrate is coated with recombinant VWF (rVWF-12) in 0.1 M carbonate at pH 9.6. The samples are diluted in PBS-gelatin buffer incubated with the wells and subsequently with a goat anti-rabbit IgG-HP antibody (SIMIT). The PEGylation of VWF is determined as an increase in molecular weight confirmed by SDS-PAGE. The binding of the antibodies present in the serum samples to PEGylated recombinant VWF (rVWF) is detected. No binding of the antibodies present in the serum samples to rVWF is observed (FIG. 4A).

Figure 4B:
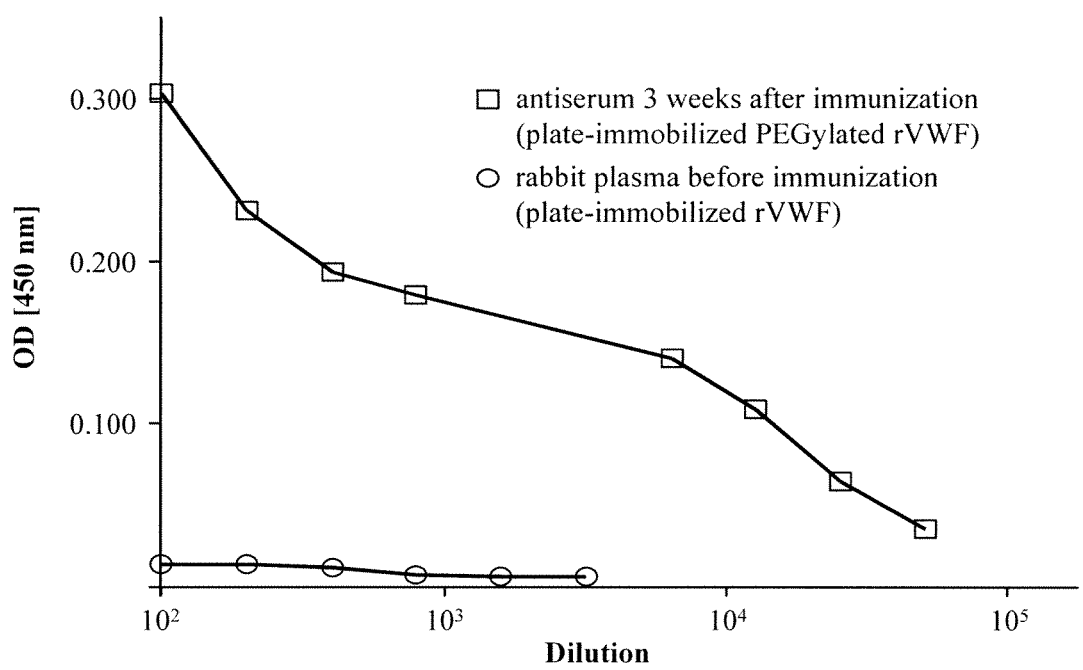

More specifically, rabbit serum samples (see Example 1) were allowed to react with plate-immobilized rVWF and PEGylated rVWF. PEGylated rVWF was prepared by using the PEGylation reagent as described by Kozlowski et al (BioDrug 5: 419-29, 2001). Both proteins were coated to polystyrene plates (Example 1). The rabbit serum samples, taken before the immunization and after 3 weeks, were diluted in PBS-gelatin buffer, incubated with the wells and subsequently with a goat anti-rabbit IgG-HRP antibody. The binding of the IgG present in the rabbit serum samples to plate-immobilized PEGylated rVWF was detected, although the rabbits were immunized with PEGylated hSA. No binding of the IgG present in the rabbit serum samples to rVWF was observed (FIG. 4B).

These experiments demonstrate that the anti-PEG antibodies do not non-specifically bind non-PEGylated protein.

Example 5

ELISA for the Detection of VWF-PEGylation

To determine the ability of the anti-PEG antibody to detect PEGylated protein, such as PEGylated VWF, a VWF-PEG ELISA was developed.

Figure 5A:
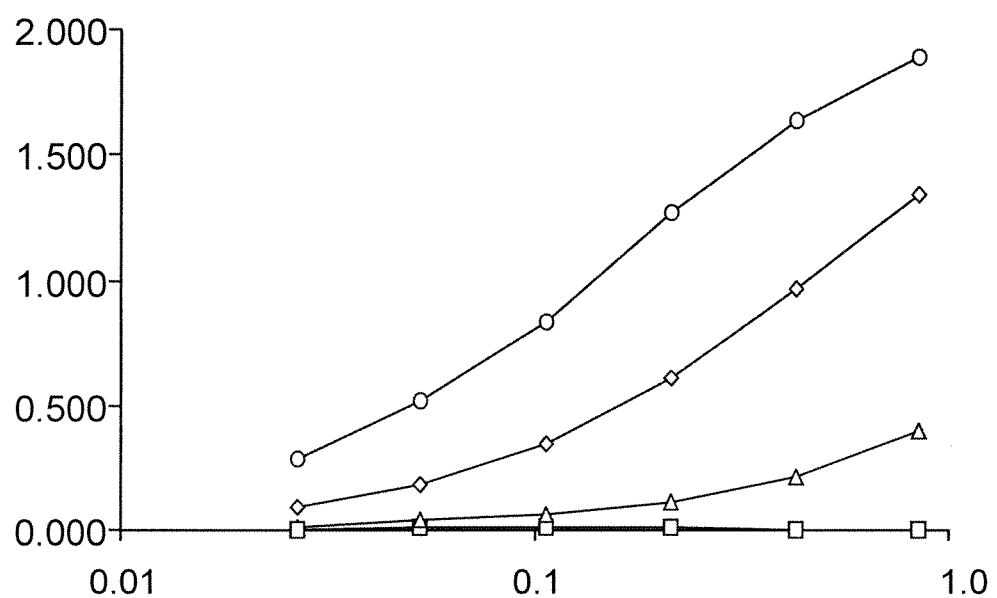
FIG. 5 shows the ELISA for the detection of VWF-PEGylation. A substrate (NUNC Maxisorp F96) was coated with anti-VWF antibody and incubated with decreasing amounts of PEGylated VWF followed by an incubation with an anti-PEG peroxidase conjugate. The bound peroxidase was detected by a color reaction with SureBlue and the signal intensity is correlated with the concentration of PEGylated VWF in the dilution. The optical density (OD) (vertical axis) is shown for the log mU anti-VWF antibody/ml dilution (horizontal axis) of the respective samples. ■, wP-005-1-SS a (A); ▲, wP-005-1-SS e (E); ◊, wP-005-1-SS f (F); ●, wP-005-1-SS g (G). Sample A represents the native rVWF before modification whereas the preparations E, F and G were prepared using the PEGylation reagent PEG-SS-5K in the molar concentrations of 1 mM, 2.5 mM and 7.5 mM.
Figure 5B:
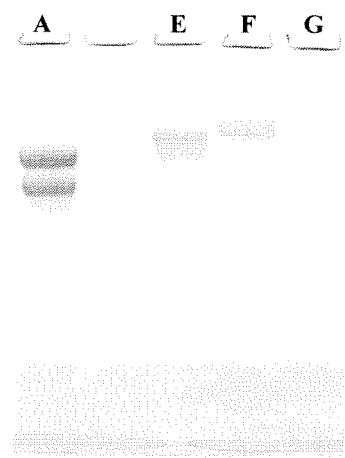
Figure 5C:
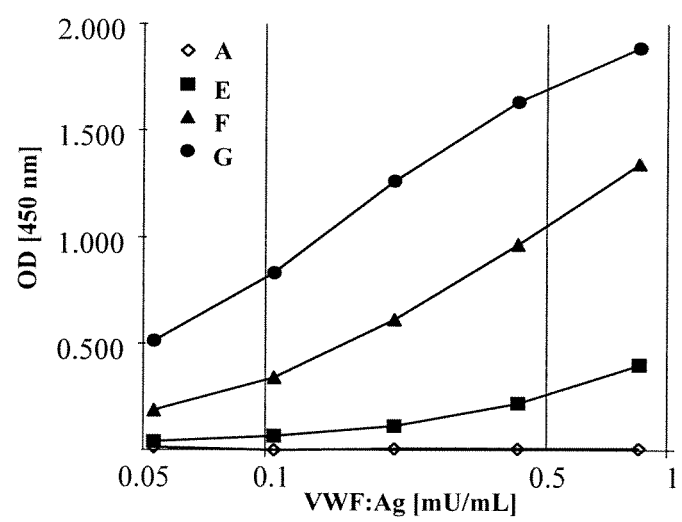

In brief, a substrate (NUNC Maxisorp F96) is coated with anti-VWF antibody and incubated with decreasing amounts of PEGylated VWF followed by an incubation with an anti-PEG peroxidase conjugate. The bound peroxidase is detected by a color reaction with SureBlue and the signal intensity is correlated with the concentration of PEGylated VWF in the dilution (FIG. 5).

More specifically, the following example describes a protein-PEG ELISA that uses a protein-specific antibody, preferably derived from rabbit, in combination with an enzyme-conjugated anti-PEG IgG, preferably derived from rabbits, for the detection and the measurement of a PEGylated protein. Basically, the PEGylated protein is captured by the plate-immobilized anti-protein antibody and then allowed to react with an anti-PEG IgG-peroxidase conjugate. Rabbit anti-human VWF (DakoCytomation A-0082) was diluted 1/500 in sodium carbonate buffer, pH 9.6 and coated to a polystyrene plate (Example 1). Alternatively, any monoclonal antibody can be used in an appropriate dilution. Washing was done with PBS, the dilution buffer contained gelatin at 5 mg/mL. rVWF (sample A) and various PEGylated rVWF preparations (samples E, F, G) were diluted with dilution buffer to a VWF:Ag concentration of 0.85 mU/mL. Sample A represents the native rVWF before modification whereas the preparations E, F and G were prepared using the PEGylation reagent PEG-SS-5K in the molar concentrations of 1 mM, 2.5 mM and 7.5 mM. Five further 1+1 dilutions were prepared and incubated with the plate-immobilized anti-VWF IgG. Bound PEGylated rVWF was detected by reaction with the anti-PEG IgG peroxidase conjugate and the peroxidase substrate SureBlue. Table 2 shows the slopes and the regression coefficients for the dose-response curves of the different preparations measured. Obviously, non-PEGylated rVWF (sample A) showed no response, whereas the linear dose-response curves of the three PEGylated rVWF samples E, F and G had clearly differing slopes.

TABLE 2

Slope and correlation coefficients of dose-response curves of the rVWF-PEG ELISA

|  | Sample A | Sample E | Sample F | Sample G |
|---|---|---|---|---|
| slope | 0.000 | 0.4771 | 2.0523 | 4.6259 |
| correlation coefficient | n.a. | 1.000 | 0.992 | 0.995 |

The three PEGylated rVWF preparations showed increased molecular weight on SDS PAGE (FIG. 5) as compared to the non-PEGylated rVWF. In addition, higher PEG to rVWF ratios applied for the PEGylation resulted in increased molecular weights of the PEGylated rVWF preparations and in steeper dose-response curves. Thus, the design described not only specifically detected protein-bound PEG, but also allowed the differentiation of preparations with different degrees of PEGylation.

Example 6

Specificity of the rVWF-PEG ELISA as Shown by the Inhibition with PEG

In order to assess the specificity of the PEG assay, an inhibition study study was carried out.

Figure 6:
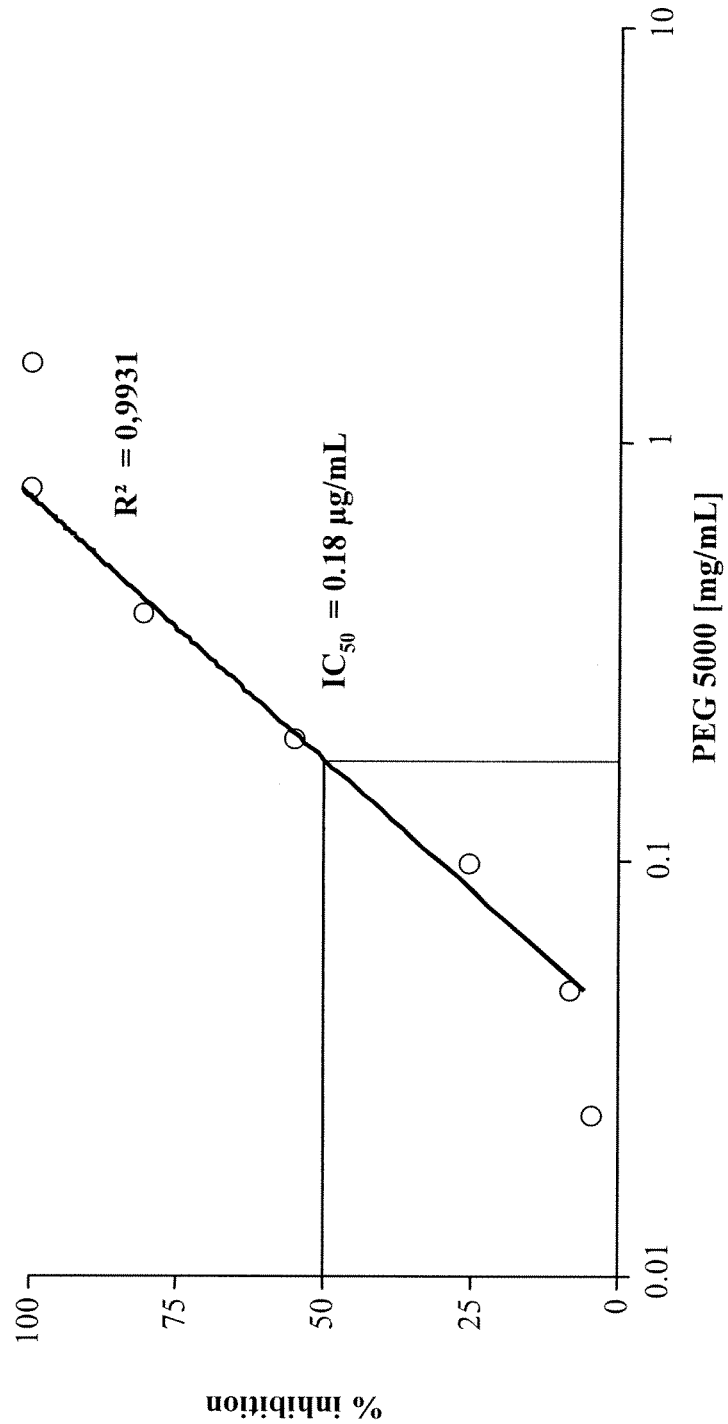
FIG. 6 shows inhibition of the rVWF-PEG detection when free PEG 5000 is added to the culture.

The assay was done as described above (see Example 5) using the PEGylated rVWF preparation G with the highest degree of PEGylation. The diluted PEGylated rVWF sample (0.85 mU/mL) was incubated with the plate-immobilized anti-VWF antibody and then with the anti-PEG IgG-peroxidase conjugate in the presence of PEG 5000 (50 mg/mL to 0.024 mg/mL). PEG 5000 causes a clear dose-dependent inhibition (FIG. 6) with an $IC_{50}$ of 0.18 μg/mL.

Example 7

Description of a PEG-PEG ELISA

This example describes a PEG-PEG ELISA that uses the polyclonal rabbit anti-PEG IgG for capturing and detecting PEGylated proteins or free PEG.

Figure 7:
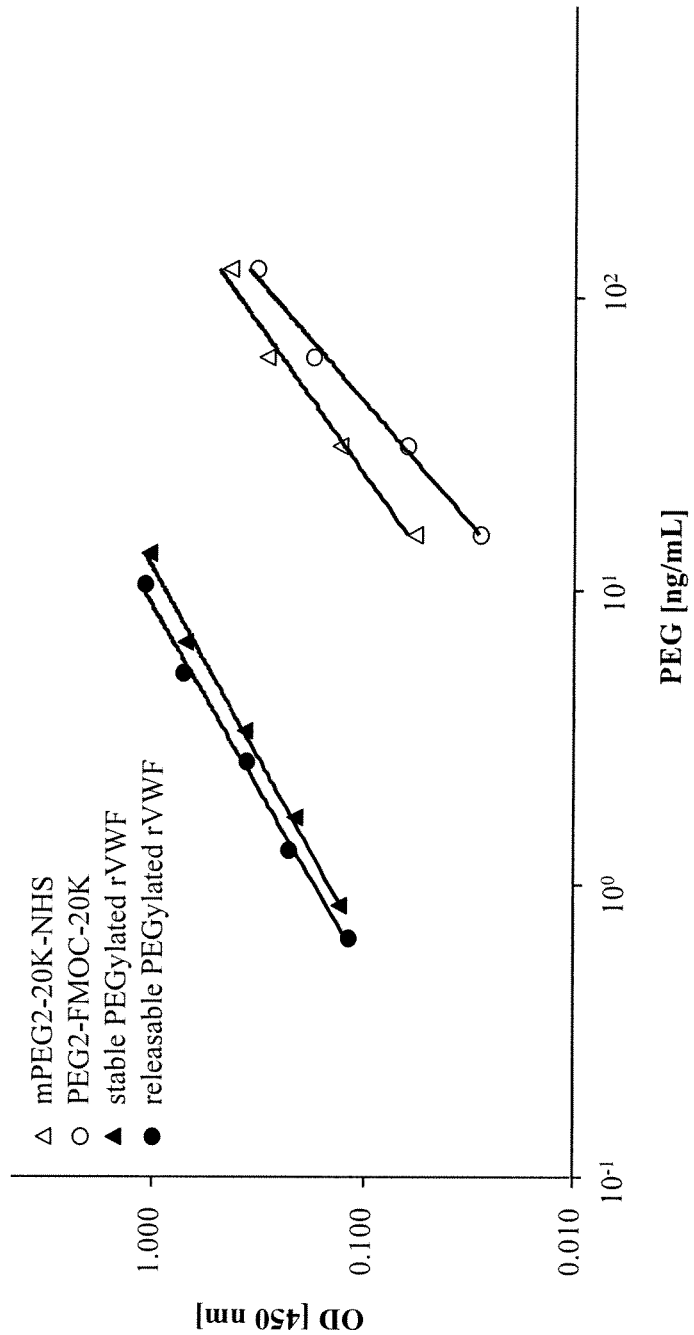
FIG. 7 shows dose-response curves of a PEG-PEG ELISA.

Anti-albumin-depleted rabbit anti-PEG IgG was coated in 0.1 M sodium carbonate, pH 9.6 overnight to polystyrene plates (Example 1). The blocking of the plates was done with PBS, pH 6.1 containing 2% non-fat dry milk and 2 mM benzamidine, at 37° C. for 3 hours. Tween 20 or other polyethoxy-containing detergents were not used for the whole assay. Blocking buffer was used to prepare dilution series for the following samples: mPEG2-20K-NHS (stable 20K PEGylation reagent as described by Kozlowski et al [Biodrug 2001; 5: 419-29]) and stable PEGylated rVWF (9.8 μg bound PEG per IU VWF:Ag), prepared by using this reagent; 20K-PEG2-FMOC-NHS (branched "releasable" 20K PEG reagent, as described in US2008/0234193) and releasable 20K-PEGylated rVWF (8.2 μg bound PEG per IU VWF:Ag) prepared by using this reagent. The PEG reagents were dissolved in distilled water at a concentration of 10 mg/mL and kept at room temperature overnight to hydrolyze the active N-hydroxysuccine imide (NHS) group. The samples' dilutions were allowed to bind to the plate-immobilized anti PEG antibody at room temperature for 1 hour. The plates were then washed and anti-PEG IgG peroxidase was applied. Finally, bound peroxidase activity was measured. All samples showed linear dose-response curves (FIG. 7), although with different sensitivities. The PEGylated rVWF preparations could be measured in the low ng range of bound PEG. The non-conjugated free PEG reagents after hydrolysis could also be measured with this assay design but higher PEG concentrations were required for the linear dose-response relation.

These findings demonstrated that the anti-PEG IgG obtained by immunization of rabbits with 5K PEGylated hSA (i) binds not only to 5 k PEG used for the immunization and (ii) binds to a repeating epitope presented on the PEG chain and not to the protein-PEG linkage region. By employing a pretreatment for the removal of protein-bound PEG, this assay design is useful for the measurement of free, non-conjugated PEG as it remains, for example, in the reaction mixture after PEGylation. In addition, this assay is also useful to measure the amounts of non-bound PEG in the purified PEG-protein conjugate.

Example 8

Specificity of the PEG-PEG ELISA

Figure 8:
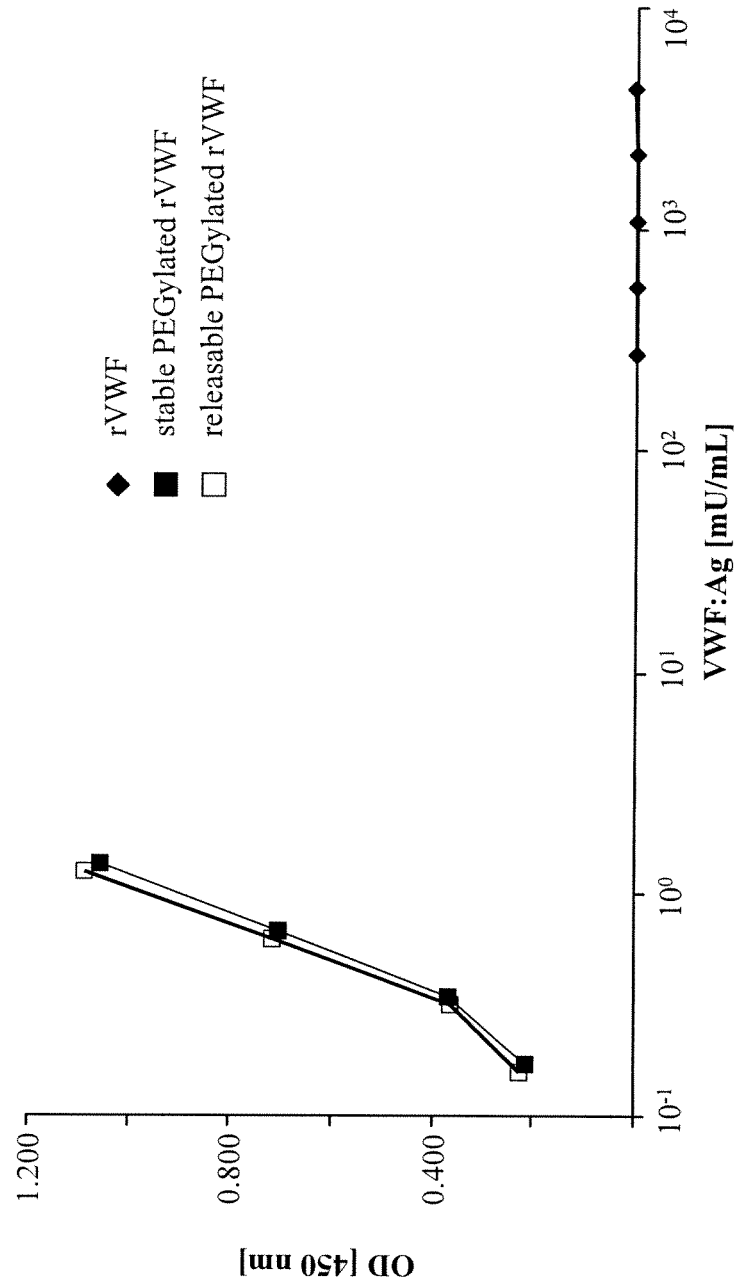
FIG. 8 illustrates the specificity of a PEG-PEG ELISA.

The specificity of the PEG-PEG ELISA described above was shown using the assay conditions described above (Example 7). In addition, a non-PEGylated rVWF sample was analyzed using the PEG-PEG assay and showed no response, even at more than 100-times higher VWF:Ag concentration (FIG. 8). These results demonstrate the specificity of the anti-PEG antibody and the PEG-PEG assay.

Example 9

Description of a PEG-Protein ELISA for the Measurement of Stable PEGylated rVWF

To determine if a PEG-specific ELISA would be a sensitive detection method when the anti-PEG antibody was used as the capture antibody, a PEG-protein ELISA was developed which uses an anti-PEG antibody for capturing the PEGylated protein and a protein-specific antibody for detecting the bound PEGylated protein.

Figure 9:
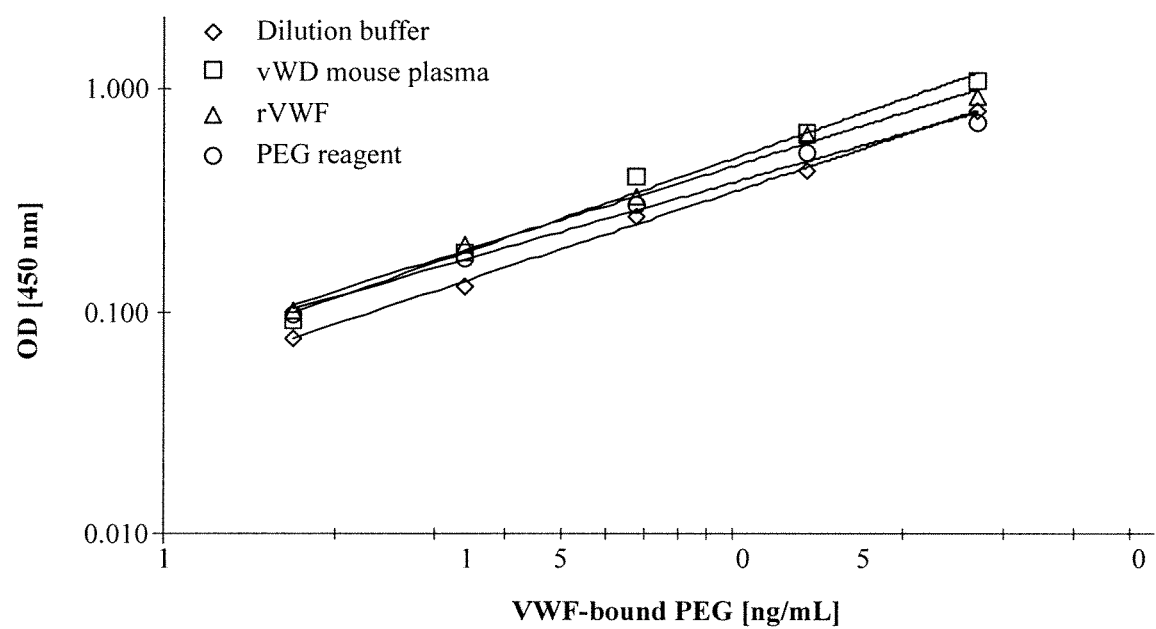
FIG. 9 shows the strong detection of PEG protein using the PEG-protein ELISA, as shown with stable PEGylated rVWF.

Albumin-depleted anti-PEG IgG was diluted to about 50 μg/mL with 0.1 M carbonate buffer, pH 9.6 and coated to the wells of 96-well polystyrene microplate (Nunc Maxisorp F96). The wells were then blocked with dilution buffer (3% non-fat dry milk in PBS, 2 mM benzamidine; pH 6.1) at 37° C. for two hours. Serial dilutions of the samples were then loaded and incubated with the wells at room temperature for 60 min. After washing, rabbit anti-human VWF-peroxidase (DakoCytomation) was added and bound peroxidase activity was measured with SureBlue. Alternatively, the peroxidase conjugate was added to the samples and incubated without a preceding washing step using the single incubation multilayer immune technique (SIMIT). A stable 20K-PEGylated rVWF preparation (see Example 7) was used. The robustness of the PEG-VWF ELISA assay was shown by diluting this preparation in Von Willebrand deficient (VWD) mouse plasma (final concentration of VWF in plasma was 90%) and by the addition of PEG reagent (final concentration of PEG reagent: 1 mg/mL at 0.5 IU PEGylated VWF) as described in Example 7 and rVWF (final concentration of rVWF: 7 IU at 5 IU PEGylated rVWF). Linear dose-response curves were obtained for all samples in the range of 27 to 1.7 ng/mL bound PEG (FIG. 9) when using the sequential assay format, but also for the SIMIT format.

Neither the presence of non-conjugated PEG reagent nor a surplus of non-PEGylated rVWF impaired the assay. Also, the matrix of VWD mouse plasma did not interfere. Thus, the assay demonstrates robust and sensitive detection of PEG-protein conjugates Example 10

Figure 10:
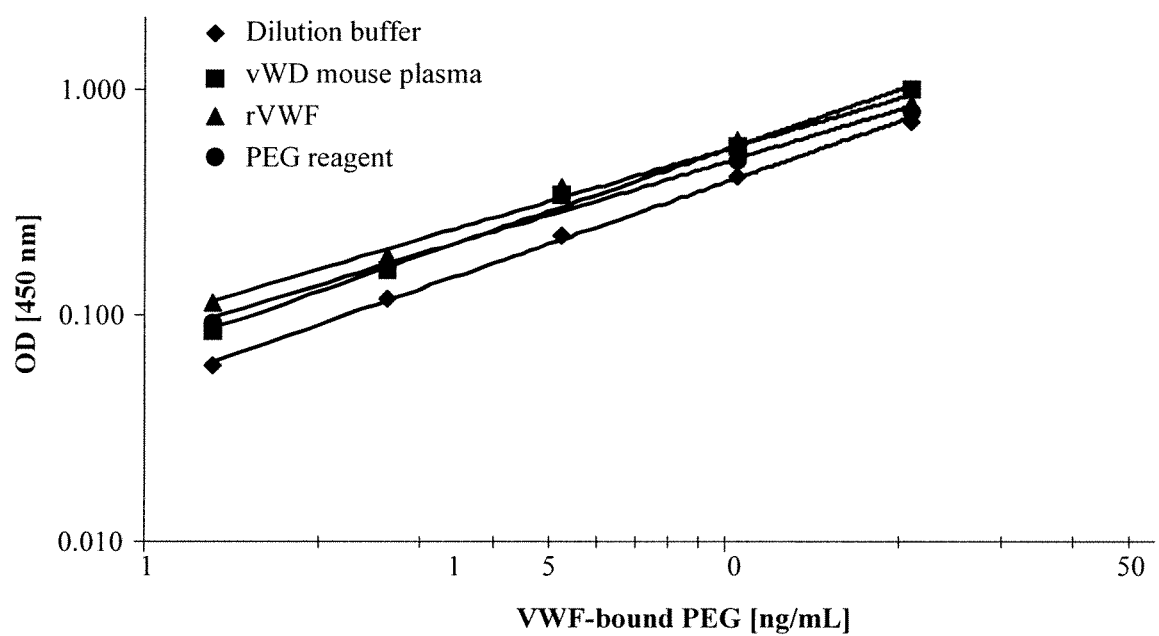
FIG. 10 illustrates the strong detection of PEGylated protein using the PEG-protein ELISA, as shown with releasable PEGylated rVWF.

Description of a PEG-Protein ELISA for the Measurement of Releasable PEGylated rVWF The robustness study described above (see Example 9) was also done with a releasable 20K PEGylated rVWF preparation (see Example 7). Similar results were obtained for the releasable 20K-PEGylated rVWF preparation with a linear range of 21 to 1.3 ng/mL (FIG. 10) and no interference of any of the compounds was detected. These data demonstrated that the linker used to attach the PEG moiety to the protein had no impact on the detection/measurement of the PEG-protein conjugate.

Example 11

Specificity of the PEG-Protein ELISA for Protein-Bound PEG

The specificity of the PEG-protein ELISA was shown by the direct measurement of the non-conjugated PEG reagents and PEGylated rVWF preparations as described above.

Figure 11:
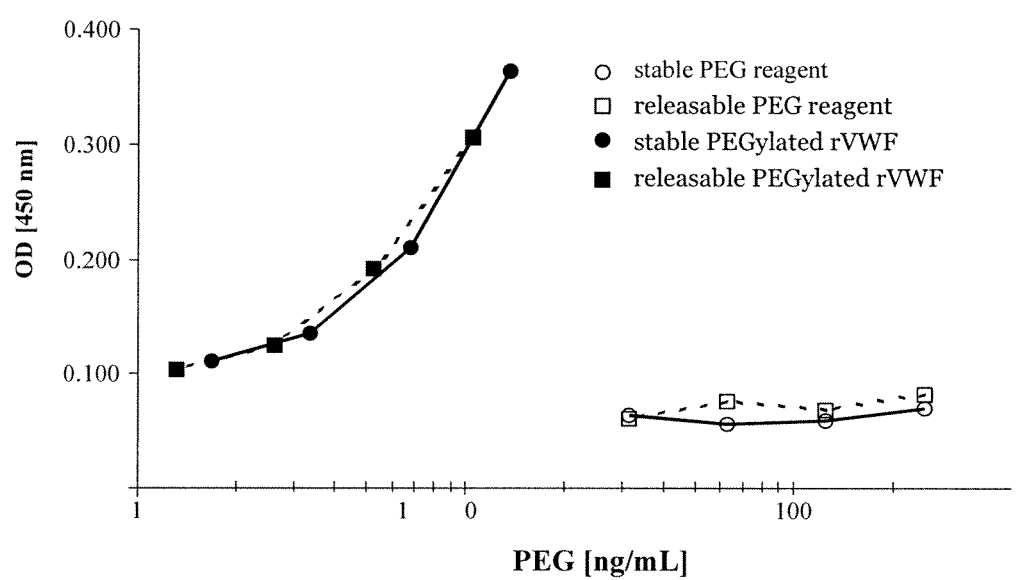
FIG. 11 illustrates the specificity of the PEG-protein ELISA for protein-bound PEG as shown with PEGylated rVWF.

In both cases, stable and releasable reagents and conjugates were used. Both PEGylated rVWF preparations showed similar, dose-dependent responses, whereas both reagents, measured at 10-times higher concentrations, did not show dose-dependent signals (FIG. 11). These data demonstrate that the PEG-protein ELISA specifically detects and measures PEG-protein conjugates.

Example 12

Specificity of a PEG-rFVIII ELISA

To determine if the PEG ELISA described herein could be used for additional blood clotting factors, the general applicable principle of the PEG-protein ELISA was shown by analyzing a PEGylated rFVIII preparation using the assay conditions as described above (Example 9).

Figure 12:
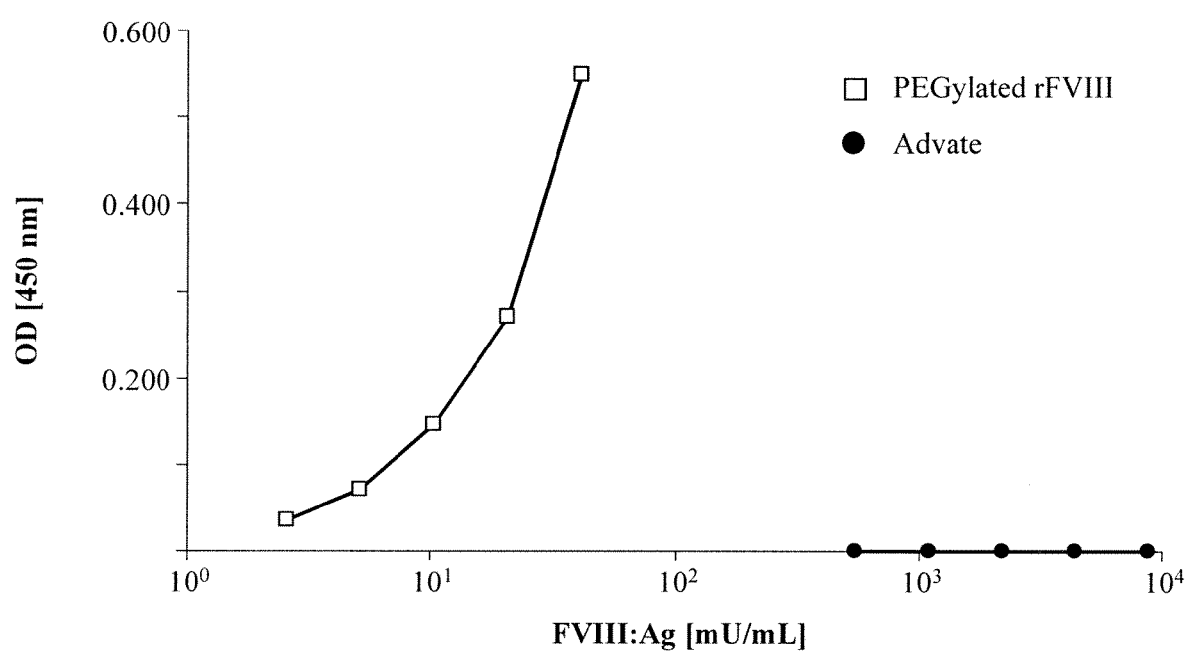
FIG. 12 shows the specificity of the PEG-rFVIII ELISA.

An anti-human FVIII peroxidase (Cedarlane) was used instead of an anti-human VWF peroxidase for detecting plate-bound PEGylated rFVIII. Results showed that the PEG-rFVIII ELISA was specific because non-PEGylated rFVIII did not show any signal even when analyzed at 1000-times higher FVIII:Ag concentrations (FIG. 12).

Example 13

PEG-rFVIII ELISA with Stable and Releasable PEGylated rFVIII

The specificity of the PEG ELISA was also measured for stable and releaseable preparations of PEG-FVIII.

Albumin-depleted anti-PEG IgG was diluted to about 50 μg/mL with 0.1 M carbonate buffer, pH 9.6 and coated to the wells of a 96-well polystyrene microplate. The wells were then blocked with dilution buffer (3% non-fat dry milk in PBS, 2 mM benzamidine; pH 6.1) at room temperature for two hours. Serial dilutions of the samples were then loaded and incubated with the wells at room temperature for 60 min. After washing, sheep anti-human FVIII-peroxidase (Cedarlane) was added and bound peroxidase activity was measured with SureBlue. A stable and a releasable 20K-PEGylated rFVIII preparation were used. These preparations had concentrations of bound PEG of 115 μg/mL and 301 μg/mL, respectively. Table 3 shows the measuring data obtained on analysis of these samples and gives the characteristics of the regression curves.

TABLE 3

PEG-rFVIII ELISA with stable and releasable PEGylated rFVIII

| Stable PEGylated rFVIII | | Releasable PEGylated rFVIII | | | | |
|---|---|---|---|---|---|---|
| | | | Day 1 | | Day 2 | |
| ng PEG/mL | OD | ng PEG/mL | plate 1 | plate 2 | plate 1 | plate 2 |
| 57.6 | 1.181 | 75.2 | 0.698 | 0.674 | 0.761 | 0.883 |
| 28.8 | 0.732 | 37.6 | 0.363 | 0.351 | 0.382 | 0.527 |
| 14.4 | 0.432 | 18.8 | 0.182 | 0.175 | 0.200 | 0.250 |
| 7.2 | 0.237 | 9.4 | 0.097 | 0.087 | 0.104 | 0.125 |
| 3.6 | 0.149 | 4.7 | 0.046 | 0.045 | 0.049 | 0.062 |
| slope | 0.7600 | slope | 0.9751 | 0.9822 | 0.9791 | 0.9740 |
| r | 0.9992 | r | 0.9997 | 0.9999 | 0.9996 | 0.9985 |

The analysis of both the stable PEGylated and the releasable PEGylated rFVIII preparation resulted in linear dose-response curves in the nanogram range of bound PEG. In addition, the assay had good reproducibility as shown for the releasable PEGylated rFVIII preparation, which allows for accurate measurement of PEGylated FVIII.

Example 14

Influence of Different Anti-FVIII Peroxidase Conjugates on the Assay Performance The influence of different anti-FVIII peroxidase conjugates on the assay performance was investigated.

Figure 13:
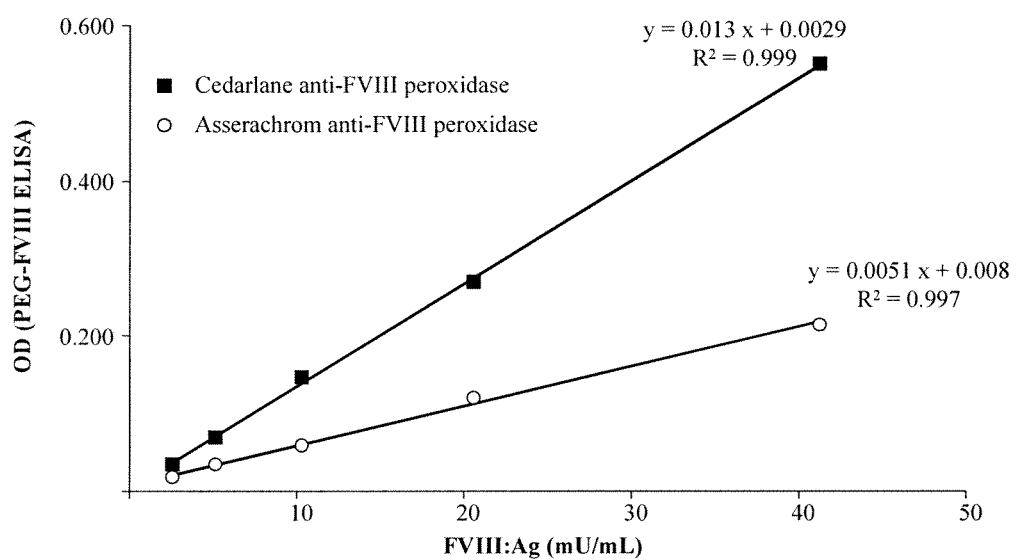
FIG. 13 is a comparison of detection of different anti-FVIII peroxidase conjugates in the PEG-FVIII ELISA assay.

The PEG-rFVIII ELISA was carried out as described above (see Example 13). Detection of anti-human FVIII peroxidase conjugates from Asserachrom and Cedarlane were compared in the same assay (FIG. 13). In both cases, linear dose-response relations were obtained between signal and FVIII:Ag levels of the samples, confirming that both conjugates could be used interchangeably.

These results suggest that the PEG ELISA is useful with any preparation of anti-protein antibody conjugate available at an appropriate selectivity.

Example 15

Performance of the PEG-FVIII ELISA in FVIII-Deficient Mouse Plasma and Rat Plasma The efficacy and sensitivity of the PEG-rFVIII ELISA was investigated in FVIII-deficient mouse plasma and in rat plasma.

A releasable PEGylated rFVIII preparation was spiked at a concentration equivalent to 0.5 μg bound PEG/mL in the plasma of the animals or in dilution buffer. The resulting dose-response curves of these samples (FIG. 14) were very similar in buffer and in the animal plasma. In addition, stable PEGylated rFVIII was spiked to FVIII-deficient mouse plasma, diluted 1/10 and 1/20, at levels of bound PEG of 50 ng/mL. Recoveries of 99.8% and 97.9% of the spiked concentrations were measured. This demonstrated that the PEG-rFVIII ELISA is useful for monitoring the pharmacokinetic of releasable PEGylated rFVIII at high sensitivity and specificity without requiring any specific sample pretreatment other than appropriate sample dilution. Similar data were obtained when samples with PEGylated rVWF were analyzed.

Example 16

Measurement of Releasable PEGylated rFVIII Preparations with Different Degree of PEGylation Releasable PEGylated rFVIII preparations with different degree of PEGylation were analyzed with the PEG-FVIII ELISA.

Figure 15:
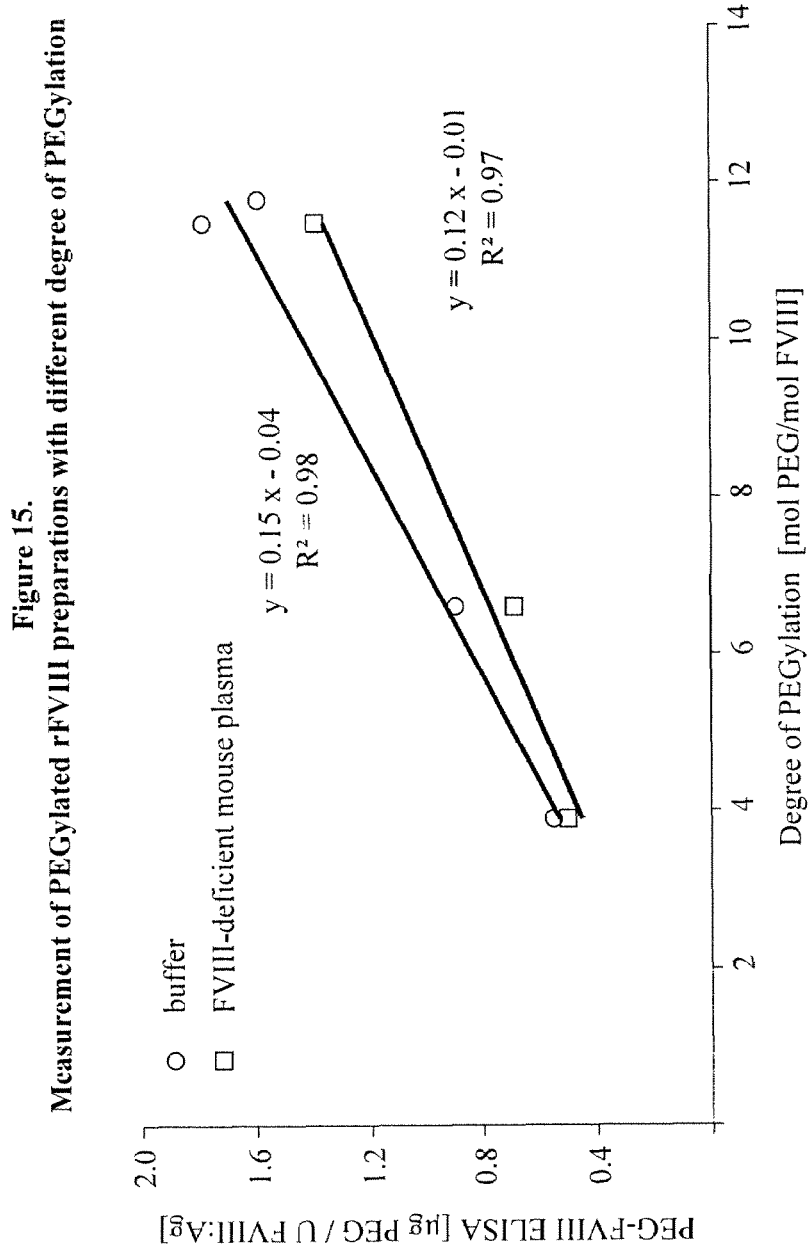
FIG. 15 is a comparison of the ELISA assay in the detection of PEGylated rFVIII preparations with different degree of PEGylation.

The ELISA was done as described above (see Example 13). In addition, the FVIII:Ag levels of these preparations were measured using a commercially available FVIII ELISA kit. The degree of PEGylation of these preparations was measured with a HPLC-based method and was expressed as mol bound PEG per mol FVIII. The PEGylated FVIII preparation was added to dilution buffer or to FVIII-deficient mouse plasma and these samples were measured with the PEG-FVIII ELISA The concentrations of bound PEG measured with the PEG rFVIII ELISA were then normalized to the FVIII:Ag concentrations of these samples and expressed as µg bound PEG per U FVIII:Ag. These FVIII:Ag-normalized PEG concentrations correlated well in buffer and in the plasma of FVIII-deficient mice with the degree of PEGylation as measured for the different preparations with the HPLC-based method (FIG. 15).

These results show that the PEG-rFVIII ELISA could discriminate between PEGylated rFVIII preparations according to their degree of PEGylation, and comparison of the absorbance of the samples to a known standard indicates the degree of PEGylation of the protein sample. Additionally, these results are achieved in buffer and also in the matrix of FVIII deficient mouse plasma as the assay does not require any specific sample pretreatement except appropriate dilution of the test samples. This provides a method to measure PEGylated protein or other PEG levels in the serum of a patient receiving PEGylated therapeutic protein.

Example 17

Influence of Free PEG on the PEG-FVIII ELISA

The possible interference of free PEG on the PEG ELISA assay was investigated in a PEG concentration range up to 1000 µg/mL.

Figure 16:
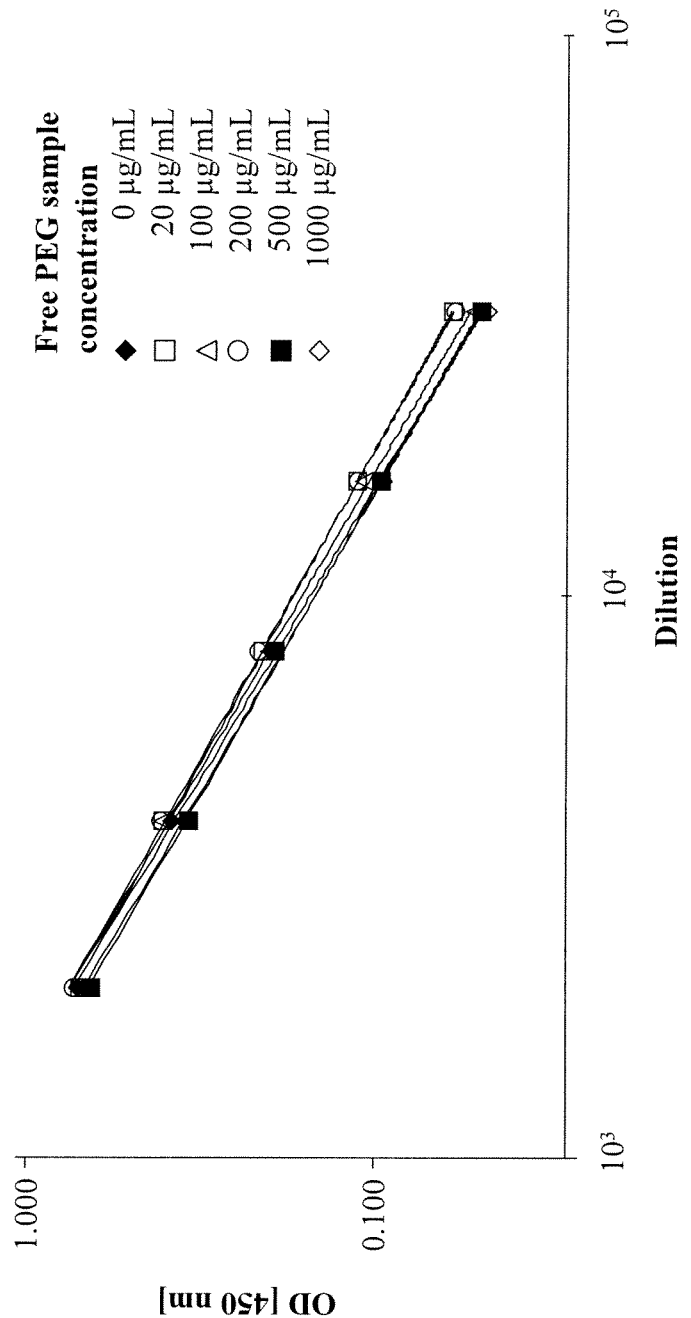
FIG. 16. shows the influence of free PEG on the PEG-rFVIII ELISA.

A releasable PEGylated rFVIII preparation was mixed with 20K-PEG2-FMOC-NHS to yield final concentrations of 20, 100, 200, 500 and 1000 µg/mL. The PEG reagent was dissolved in distilled water and kept overnight to destroy the NHS reactivity before it was added to the PEGylated rFVIII preparation. The dose-response curves obtained for these samples were highly similar (FIG. 16) and their slopes differed less than 10%.

This assays shows that even high levels of free PEG had no influence on detection levels of the PEG-rFVIII ELISA.

Example 18

Measurement of PEG Release from a Releasable PEGylated rFVIII

As shown above, the PEG ELISA measures release of the PEG polymer from the protein-PEG conjugate. To determine if the assay can measure the rate of release, a releasable PEGylated rFVIII preparation kept at conditions triggering the release of protein-bound PEG was used to measure PEG release over time.

Figure 17:
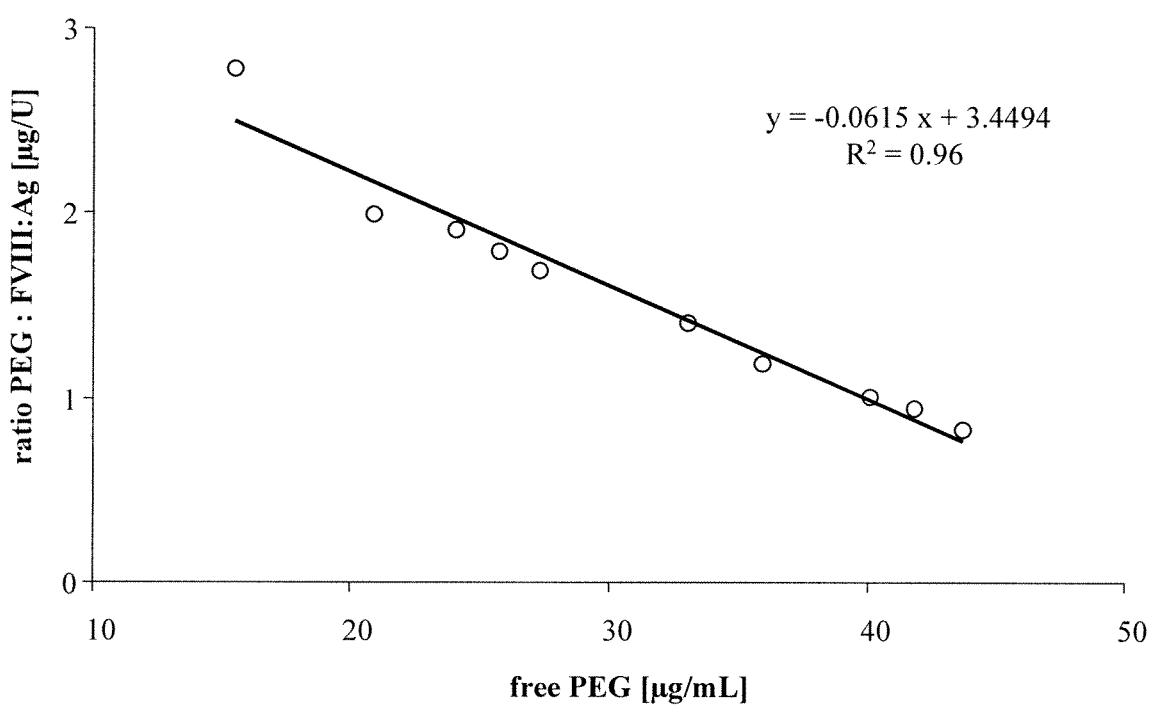
FIG. 17 depicts the ability of the PEG-rFVIII ELISA assay to measure PEG release from a releasable PEGylated rFVIII preparation and demonstrates the ELISA is capable to differentiate PEGylated FVIII molecules with different degrees of PEGylation.

The levels of free PEG were measured with size-exclusion chromatography. The levels of protein-bound PEG were measured with the PEG-FVIII ELISA and related to the FVIII:Ag concentrations of these samples. The FVIII:Ag normalized FVIII-bound PEG levels correlated well with the levels of free PEG (see FIG. 17).

These experiments demonstrated that the PEG-FVIII ELISA was capable of monitoring the release of PEG from a releasable PEGylated rFVIII preparation. This assay is useful to measure the release kinetics of PEGylated protein in vivo to patients receiving PEGylated FVIII or other PEGylated therapeutic protein.

Example 19

Detection of PEGylated rFVIIa in Normal Pooled Rat Plasma

Alternative methods to determine the levels of PEGylation of a protein or protein complex include detection of the protein-polymer complex based on molecular weight of the complex itself. This type of assay is carried out using sodium dodecylsulfate polyacrylamide gel electrophoresis (SDS-PAGE) isolation of the protein and detection of PEG molecules on the protein using an anti-PEG Western blot detection method.

To determine the detection PEGylated protein in plasma using this technique, samples of PEGylated FVIII were diluted in rat plasma and PEGylated protein levels were measured.

Samples of 20-kDa-PEG-FVIIa and 40-kDa-PEG-FVIIa were diluted to 100 µg/ml, 50 µg/ml, 25 µg/ml, 12.5 µg/ml and 6.3 µg/ml in rat plasma (Sprague Dawley), and subjected to sodium dodecylsulfate polyacrylamide gel electrophoresis (SDS-PAGE) and Western blot. Sampling buffer (NuPAGE LDS sample buffer, Invitrogen) was added to 1 µl of the product diluted in plasma and loaded onto gradient (3-8%) tris-acetate SDS polyacrylamide gels (NuPage Novex, 1.0 mm; Invitrogen). Electrophoresis was performed in tris-acetate SDS running buffer under non-reducing conditions. Proteins were blotted for 16 hours with 1.25 W at +4° C. onto polyvinylidene difluoride (PVDF, 0.2 µm) membranes (Sequi-Blot PVDF membrane, BIO-RAD, Richmond, Calif., USA). Afterwards, membranes were blocked in casein-TBS solution (Pierce, Rockford, Ill., USA) for 1 hour at +37° C.

Afterwards, the immunoblots were incubated with the monoclonal rabbit anti-PEG antibody (Epitomics, Calif., USA), diluted 1/1000 for 2 hours at room temperature. The antibody was diluted in TBS+0.05% Tween20 (TBST)+10% casein-TBS. After 5 washing steps with TBST, each for 10 minutes, the secondary antibody goat anti-rabbit IgG (H+L)-horseradish peroxidase (HRP) conjugate was applied (DAKO Cytomation, Glostrup, Denmark), diluted 1/1000 in TBST/10% casein-TBS, for 1 hour at room temperature (RT). After 5 washing steps with TBST, the blots were developed using the enhanced chemiluminescence (ECL) Plus Detection Kit according to the manual of the manufacturer (GE Healthcare, Buckinghamshire, UK).

Figure 18:
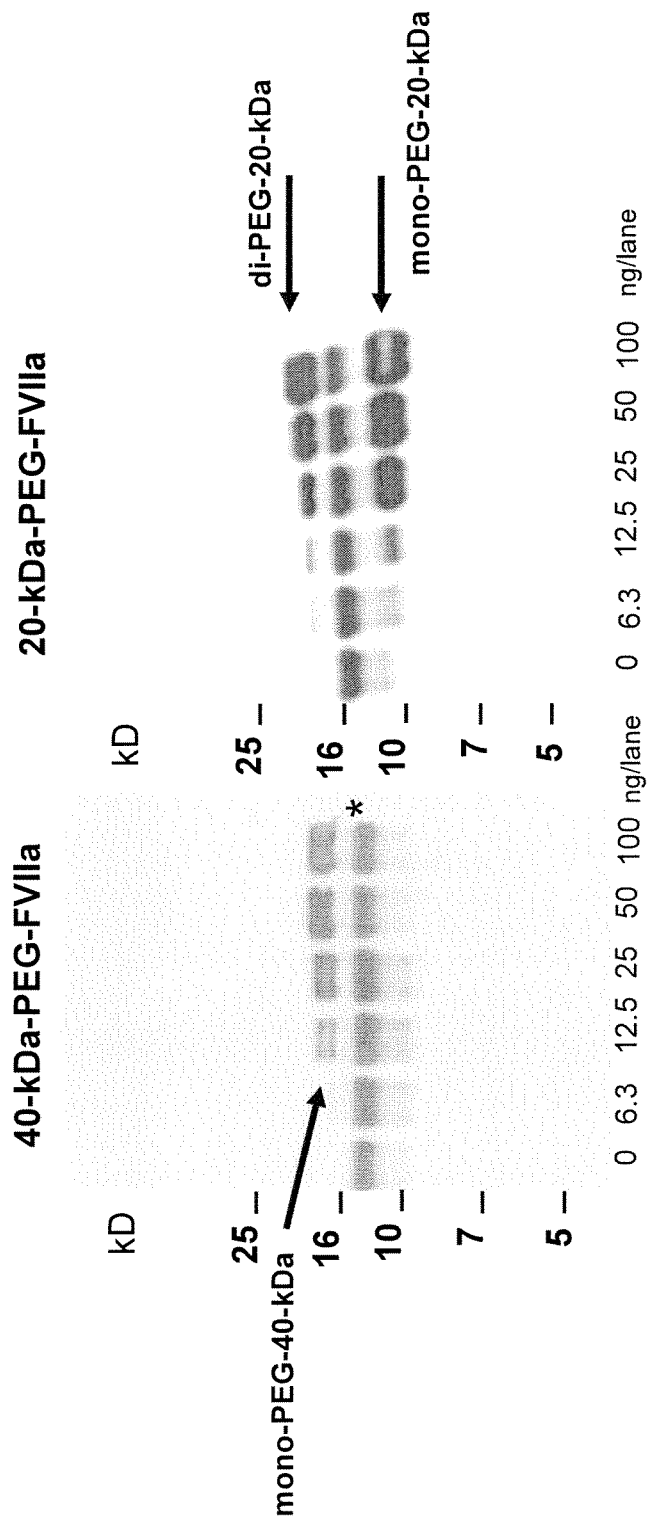
FIG. 18 shows that PEGylated protein was detectable using the sensitive ECL method in all applied concentrations.

For the detection, a less sensitive ECL Western Blotting Reagent was used to visualize the PEGylated proteins. Even with this technique, the PEGylated protein was detectable in all applied concentrations. The secondary antibody showed a cross-reaction with the rat immunoglobulins (band marked with * in FIG. 18). This cross reaction could be avoided by immunodepletion of the rat plasma for the immunoglobulin prior application to the gel.

Example 20

Detection of PEGylated rFVIIa in Normal Human Plasma

To determine the detection of PEGylated protein in human plasma, samples of PEGylated FVIII were diluted and PEGylated protein levels were measured.

Samples of 20-kDa-PEG-FVIIa was diluted to 5 μg/ml and 2.5 μg/ml in pooled normal human (George King Bio-Medical) plasma or in 5% HSA/HNa buffer (25 mM HEPES, 175 mM NaCl, pH 7.35). The ECL plus detection system was used and the film was exposed for a very short (30 seconds) time (FIG. 2B). For these samples, SDS-PAGE using a 3-8% tris-acetate gradient gel was followed by Western blot analysis. The ECL Plus Detection System was used to visualize the bands.

Figure 19A:
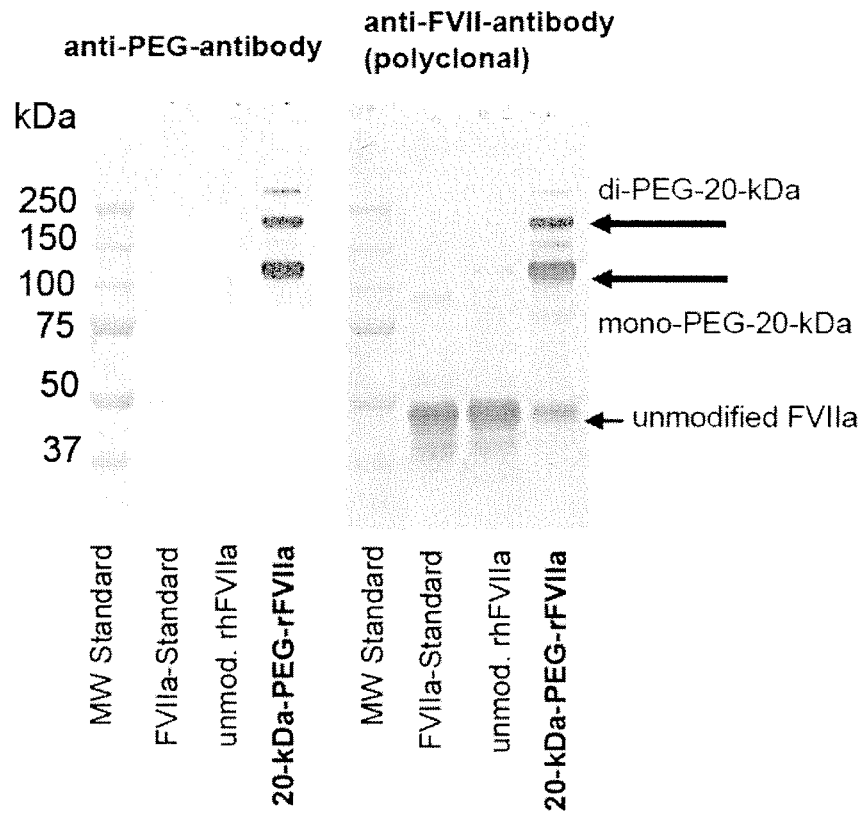
FIG. 19 is a comparison of the levels of detection of PEGylated protein diluted in buffer (FIG. 2A) or in human plasma (FIG. 2B).
Figure 19B:
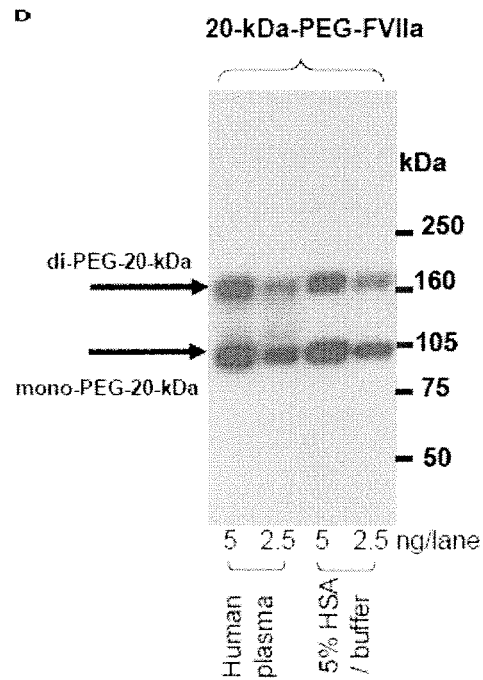

For comparison, SDS-PAGE using 4-12% bis-tris gradient gels followed by Western blot analysis of 100 and 50 ng of 20-kDa-PEG-FVIIa detected with anti-PEG antibody (diluted 1/300 in TBS/0.05% non fat dry milk (BIO-PAD)) and a polyclonal sheep anti-human FVII antibody (Affinity Biologicals, ON, Canada), diluted 1/2000 in TBST/0.1% non fat dry milk. An alkaline phosphatase (ALP) system was applied to visualize the proteins (FIG. 19A).

There was no difference detectable whether the PEGylated rFVIIa was diluted in buffer or in plasma, and only a weak cross reaction with the human plasma was observed (FIG. 199B). These results demonstrate that the method is appropriately sensitive to detect low levels of conjugated protein in a sample comprising many different proteins, such as human plasma, and is therefore useful to detect polymer-conjugated protein a sample taken from a patient receiving blood clotting factor to treat a clotting disorder.

Example 21

Detection of In Vitro PEG-Release of 20-kDa-PEG-rFVIIa in Normal Human Plasma PEGylation usually decreases the protein's biological function. However, modifying the proteins with a reversibly-linked PEG, which has the potential to dissociate from the protein over time should allow liberation of the native protein, accompanied with full restoration of its activity. This process is monitored by measuring the increase of activity in the plasma over time. However, the measured activity is depending on the rate of release reaction and inactivation/elimination of the protein. This invention is also suitable to measure the structural changes including de-PEGylation of such a protein in a plasma matrix.

Figure 20:
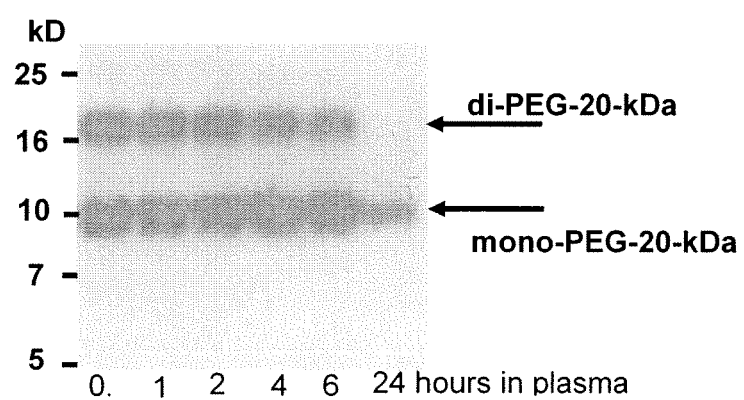
FIG. 20 illustrates that the method detects the change in degree of PEGylation of the PEGylated rFVIIa over time.

The releasable 20-kDa-PEG-rFVIIa conjugate was diluted to 0.023 μg/ml in normal human plasma and incubated for 24 hours at 37° C. The release of the PEG molecule was determined by SDS-PAGE and Western Blot analysis using the specific anti-PEG antibody as described in Example 1. As shown in FIG. 20 the amount of di-PEGylated rFVIIa slightly decreases over time and completely disappears after 24 hours incubation. In contrast, the mono-PEG species shows a slight increase first and is still present after 24 hours. Thus, the methods detects sequential de-PEGylation of the protein molecule.

These results illustrate that the present method allows for the determination of the degree of water soluble polymer of the surface of a protein or protein complex, and also allows for a determination of the mechanism of release of a releasable water-soluble polymer from the protein.

Example 22

Detection of PEGylated FVIII in Normal Human Plasma

To determine the ability of the present assay to detect a change in the degree of PEGylation, two FVIII samples conjugated with different PEG reagents exhibiting a differing PEGylation degree were diluted in human plasma and the detection of the molecules measured.

Samples were diluted in the range of 5 to 1 μg/ml and loaded onto 3-8% gradient tris-acetate SDS-polyacrylamide gels followed by Western blot analysis. The PEGylation degree (PD) of the stable 20-kDa PEG-FVIII conjugate is 3.7 (FIG. 21A), that of the releasable one with the same PEG type is 6 (FIG. 21B).

As shown in FIG. 21, a higher PEGylation degree resulted in a stronger signal using the same development conditions.

These results show that the new method to trace PEGylated proteins in pharmacokinetic studies described herein can detect changes in their domain structure and PEGylation degree.

Numerous modifications and variations in the invention as set forth in the above illustrative examples are expected to occur to those skilled in the art. Consequently only such limitations as appear in the appended claims should be placed on the invention.

We claim:

1. A method for determining the number of polyethylene glycol (PEG) polymer molecules in a polymer:protein conjugate having one or more PEG polymer molecules bound to the protein, the method comprising:
   contacting the polymer:protein conjugate with an antibody that specifically binds the PEG polymer of the polymer:protein conjugate, the antibody detectable when bound to the polymer:protein conjugate,
   detecting the level of the antibody bound to the polymer:protein conjugate,
   wherein the number of PEG polymer molecules in the polymer:protein conjugate correlates with the level of the antibody detected bound to the polymer:protein conjugate when compared to a known control, and wherein antibody binding is dose dependent and linear with respect to an amount of bound PEG.

2. The method of claim 1, wherein the PEG is from 3 to 100 kDa.

3. The method of claim 2, wherein the PEG has a molecular weight in a range of about 5 kDa to about 60 kDa.

4. The method of claim 2, wherein the PEG has a molecular weight in a range of about 5 kDa to about 40 kDa.

5. The method of claim 2, wherein the PEG has a molecular weight in a range of about 5 kDa to about 15 kDa.

6. The method of claim 2, wherein the PEG has a molecular weight in a range of about 5 kDa to about 10 kDa.

7. The method of claim 1, wherein the antibody comprises a detectable label.

8. The method of claim 1, wherein the polymer:protein conjugate is bound to a carrier matrix prior to binding with the antibody.

9. The method of claim 8, wherein the level of antibody detected is measured as absorbance of the detectable label.

10. The method of claim 1, wherein the polymer:protein conjugate is isolated using sodium dodecylsulfate polyacrylamide gel electrophoresis (SDS-PAGE) and transferred to a membrane prior to the detecting.

11. The method of claim 10, wherein the number of polymers in the polymer:protein conjugate is calculated based on the molecular weight of the protein-polymer conjugate compared to a known control.

12. The method of claim 10, wherein the molecular weight of the polymer-protein complex correlates with the protein subunit comprising the polymer molecule.

13. The method of claim 1, wherein the protein or protein complex is a blood clotting factor or a blood clotting factor complex.

14. The method of claim 13 wherein the blood clotting factor or blood clotting factor complex is human.

* * * * *